US009078574B2

(12) United States Patent
Snell et al.

(10) Patent No.: US 9,078,574 B2
(45) Date of Patent: Jul. 14, 2015

(54) SYSTEMS AND METHODS FOR OFF-LINE REPROGRAMMING OF IMPLANTABLE MEDICAL DEVICE COMPONENTS TO REDUCE FALSE DETECTIONS OF CARDIAC EVENTS

(71) Applicant: PACESETTER, INC., Sylmar, CA (US)

(72) Inventors: Jeffery D. Snell, Chatsworth, CA (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 14/137,308

(22) Filed: Dec. 20, 2013

(65) Prior Publication Data

US 2014/0114203 A1 Apr. 24, 2014

Related U.S. Application Data

(62) Division of application No. 12/614,121, filed on Nov. 6, 2009, now abandoned.

(51) Int. Cl.
*A61N 1/00* (2006.01)
*A61B 5/04* (2006.01)
(Continued)

(52) U.S. Cl.
CPC ........... *A61B 5/04012* (2013.01); *A61B 5/0452* (2013.01); *A61N 1/3702* (2013.01); *A61N 1/37235* (2013.01); *A61B 5/0031* (2013.01); *A61B 2560/0271* (2013.01)

(58) Field of Classification Search
CPC . A61B 5/04012; A61B 5/0031; A61B 5/0452
USPC ........................................................ 607/6, 27
See application file for complete search history.

(56) References Cited

U.S. PATENT DOCUMENTS 4,768,511 A 9/1988 DeCote, Jr.
4,856,523 A 8/1989 Sholder et al.
(Continued)

FOREIGN PATENT DOCUMENTS

EP 2324763 B1 10/2012
WO 2005067790 A1 7/2005

OTHER PUBLICATIONS

Restriction Requirement, mailed Sep. 10, 2012—U.S. Appl. No. 12/614,121.

(Continued)

*Primary Examiner* — Catherine Voorhees
*Assistant Examiner* — Roland Dinga

(57) ABSTRACT

Techniques are provided for use by implantable medical devices such as pacemakers or by external systems in communication with such devices. An intracardiac electrogram (IEGM) is sensed within a patient in which the device is implanted using a cardiac signal sensing system. Cardiac events of interest such as arrhythmias, premature atrial contractions (PACs), premature ventricular contractions (PVCs) and pacemaker mediated tachycardias (PMTs) are detected within the patient using event detection systems and then portions of the IEGM representative of the events of interest are recorded in device memory. Subsequently, during an off-line or background analysis, the recorded IEGM data is retrieved and analyzed to identify false detections. In response to false detections, the cardiac signal sensing systems and/or the event detection systems of the implantable device are selectively adjusted or reprogrammed to reduce or eliminate any further false detections, including false-positives or false-negatives. Various adaptive reprogramming techniques are described.

20 Claims, 16 Drawing Sheets

(51) Int. Cl.
*A61B 5/0452* (2006.01)
*A61N 1/37* (2006.01)
*A61N 1/372* (2006.01)
*A61B 5/00* (2006.01)

(56) References Cited

U.S. PATENT DOCUMENTS

| | | | |
|---|---|---|---|
| 4,944,298 | A | 7/1990 | Sholder |
| 5,312,452 | A | 5/1994 | Salo |
| 5,334,222 | A | 8/1994 | Salo et al. |
| 5,423,867 | A | 6/1995 | Poore et al. |
| 5,431,691 | A | 7/1995 | Snell et al. |
| 5,487,752 | A | 1/1996 | Salo et al. |
| 5,891,176 | A | 4/1999 | Bornzin |
| 6,405,085 | B1 | 6/2002 | Graupner et al. |
| 6,633,776 | B2 | 10/2003 | Bevan et al. |
| 7,024,243 | B1 * | 4/2006 | Bornzin et al. .............. 607/14 |
| 7,062,328 | B1 * | 6/2006 | Levine et al. ............... 607/27 |
| 7,421,292 | B1 | 9/2008 | Kroll |
| 7,558,627 | B1 | 7/2009 | Turcott |
| 2005/0010124 | A1 * | 1/2005 | Couderc et al. ............. 600/515 |
| 2006/0235476 | A1 | 10/2006 | Gunderson et al. |
| 2008/0109041 | A1 | 5/2008 | de Voir |

OTHER PUBLICATIONS

Restriction Requirement, mailed Feb. 15, 2013—U.S. Appl. No. 12/614,121.
NonFinal Office Action, mailed Apr. 4, 2013—U.S. Appl. No. 12/614,121.
Final Office Action, mailed Sep. 27, 2013—U.S. Appl. No. 121614,121.

* cited by examiner

SYSTEMS AND METHODS FOR OFF-LINE REPROGRAMMING OF IMPLANTABLE MEDICAL DEVICE COMPONENTS TO REDUCE FALSE DETECTIONS OF CARDIAC EVENTS

CROSS REFERENCE TO RELATED APPLICATIONS

This application is a division of U.S. patent application Ser. No. 12/614,121, filed Nov. 6, 2009.

FIELD OF THE INVENTION

The invention relates generally to implantable medical devices such as pacemakers and implantable cardioverter-defibrillators (ICDs) and, in particular, to techniques for reprogramming components of the devices employed to detect abnormal cardiac events such as arrhythmias.

BACKGROUND OF THE INVENTION

Implantable medical devices such as pacemakers and ICDs are typically configured to sense electrical cardiac signals within a patient as intracardiac electrograms (IEGMs). An IEGM is representative of electrical signals emitted by active cardiac tissue as detected by electrodes placed in, on or near the heart. The IEGM is then used to control the operation of the device. For example, the IEGM may be examined to detect arrhythmias or other abnormal cardiac events such as premature atrial contractions (PACs) and premature ventricular contractions (PVCs) so that appropriate thereby can then be delivered to the patient by the device. The portions of the IEGM that correspond to abnormal cardiac events are preferably digitized and recorded within the implanted device, along with an indication of the date and time, for eventual transmission to an external programmer for display thereon, typically during follow-up sessions with a clinician. The clinician can then review the IEGMs recorded within the patient during the abnormal cardiac events to verify that the events were indeed abnormal and to confirm that appropriate therapy was delivered. The clinician can also reprogram the device, if warranted.

The implanted device is also equipped to detect various normal cardiac events within the IEGMs, such as atrial depolarization events (P-waves), ventricular depolarization events (R-waves or QRS-complexes), ventricular repolarization events (T-waves) and to generate event marker codes representative of these and other events for recording within device memory for eventual transmission to the external programmer. The external programmer then generates event marker icons based on the event code and displays the icons along with the IEGM signals. Exemplary event markers are: "P" for a sensed depolarization event in the atria; "R" for a sensed depolarization event in the ventricles; "A" for a paced depolarization event in the atria, and "V" for a paced depolarization event in the ventricles. Along with event markers, the programmer may also display numerical values indicative of heart rate or indicative of various measured intervals between atrial and ventricular events, based on still further IEGM information recorded and transmitted by the implantable device.

U.S. Pat. No. 5,431,691, to Snell et al., entitled "Method and System for Recording and Displaying a Sequential Series of Pacing Events" provides a description of the operation of an exemplary pacemaker and external programmer, including a detailed description of the generation, transmission and display of IEGM data and event markers. See, also, U.S. patent application Ser. No. 11/740,720, now U.S. Pat. No. 7,778,699, of Ferrise et al., entitled "System and Method for Trigger-Specific Recording of Cardiac Signals using an Implantable Medical Device." See, also, U.S. Pat. No. 6,633,776 to Levine et al., entitled "Method and Apparatus for Generating and Displaying Location-Specific Diagnostic Information using an Implantable Cardiac Stimulation Device and an External Programmer." Herein, IEGMs, corresponding event markers, and any other pertinent data stored therewith are collectively referred to as "IEGM data."

Current state-of-the-art devices permit IEGMs to be sensed and recorded using several possible electrode configurations. For example, one IEGM might be derived from voltage signals sensed between the right ventricular (RV) tip electrode and the RV ring electrode; whereas another IEGM might be derived from voltage signals sensed between the right atrial (RA) tip electrode and the housing or "can" of the device itself. Each electrode combination thereby provides a different representation of the electrical conditions of the heart, which is particularly helpful to the clinician. In this regard, if the patient is subject to atrial arrhythmias, it may be advantageous to specifically examine atrial IEGM data, such as an $A_R$ TIP-can IEGM; whereas, if the patient is subject to ventricular arrhythmias, it may instead be advantageous to examine ventricular IEGM data, such as a $V_R$ TIP-$V_L$ TIP IEGM. Lead systems often include numerous electrodes, thereby providing a wide range of choices of electrode pairs for recording IEGMs. In addition to the aforementioned $A_R$ TIP, $V_R$ TIP, $V_L$ TIP and device housing electrodes, lead systems for use with state-of-the-art devices may include: a right atrial ring electrode ($A_R$ RING), a left ventricular tip electrode ($V_L$ TIP), a left atrial ring electrode ($A_L$ RING), a left atrial coil ($A_L$ COIL), a right ventricular coil ($R_V$ COIL), a left ventricular tip electrode ($V_L$ TIP), a left ventricular ring electrode ($V_L$ RING), left ventricular coil ($V_L$ COIL). Typically, IEGMs that are sensed between the device housing and one of the electrodes implanted on or within the heart, such as between the $V_R$ TIP and the device housing, are referred to as "unipolar" IEGMs. IEGMs sensed between a pair of the electrodes both implanted on or within the heart, such as between the $V_R$ TIP and the $V_R$ RING, are referred to as "bipolar" IEGMs.

As can be appreciated, given the memory and power limitations within an implantable device, it is not typically feasible to sense and record IEGM data from every possible pair of electrodes. Accordingly, clinicians are invited to select particular electrode configurations for recording IEGM data of particular interest. For example, the clinician might select two atrial channel IEGMs (i.e. IEGMs derived primarily from atrial electrodes) and two ventricular channel IEGMs (i.e. IEGMs derived primarily from ventricular electrodes) for recording. Moreover, it is not ordinarily feasible to record each of the selected IEGMs at all times. Rather it is typically feasible only to record IEGMs and corresponding event markers during periods of interest, such as during an arrhythmia or other abnormal cardiac event. Accordingly, state-of-the-art devices are configured to record the selected IEGM data only in response to the detection of arrhythmias or other anomalous events of interest (PACs, PVCs, etc.), or following an automatic mode switch (AMS) from one pacing mode to another. The events triggering the recording of IEGMs are referred to as "triggers." In state-of-the-art devices, the clinician is invited to select the particular triggers to be used by the device in activating the recording of the IEGM data.

In many cases, it is also desirable to record IEGM data prior to the trigger, as well as just following the trigger, so that the clinician can review the conditions leading up to the trigger and the conditions following the trigger. This is particularly important insofar as arrhythmias are concerned as the clinician usually wants to be able to review IEGM data prior to the onset of the arrhythmia so as to more readily diagnosis the cause of the arrhythmia. Accordingly, many state-of-the-art devices are configured to allow so-called "pre-trigger IEGMs" to be saved along with IEGMs recorded during an arrhythmia. Briefly, the device continuously detects and records IEGMs in a memory buffer, such as a circular first-in/first-out queue. If an arrhythmia is detected, the IEGMs recorded just prior to the onset of the arrhythmia are transferred from the memory buffer to long-term memory, so that the pre-trigger IEGMs can be saved along with IEGMs recorded during the arrhythmia itself for subsequent review by the clinician. In this manner, IEGM data detected during the period of time leading to the onset of the arrhythmia is saved in long-term memory for subsequent review by the clinician, without requiring all IEGMs to be saved in long-term memory at all times. Pre-trigger IEGMs can also be transferred to long-term memory upon detection of other selected triggers, such as pacemaker-mediated tachycardias (PMTs), PVCs, AMS events, etc. A particularly effective technique for implementing pre-trigger memory is set forth in U.S. Pat. No. 7,421,292 to Kroll, entitled "System and Method for Controlling the Recording of Diagnostic Medical Data in an Implantable Medical Device."

Thus, state-of-the-art implantable medical devices provide for the recording of pre-trigger and post-trigger IEGMs upon detection of particular diagnostic triggers chosen by the clinician or other clinician. Moreover, the clinician can also specify the particular electrode pairs for use in sensing the IEGMs to be recorded. This provides considerable flexibility to the clinician in obtaining IEGMs of interest while also reducing the amount of data the device itself needs to record. However, there is considerable room for further improvement.

It has been found that a large amount of stored IEGM data is falsely triggered, i.e., the "abnormal" events triggering the recording of IEGM data are often not actual abnormal events. For example, events initially deemed to be PACs or PVCs might instead have just been the result of far-field sensing of P-waves or R-waves (FFRWs) from other cardiac chambers. Since stored IEGMs typically require a significant amount of memory, such "false positives" can result in the use of substantial device memory to store unhelpful or useless information. Worse, in at least some cases, a false detection can result in the delivery of unneeded or inappropriate therapy.

In other cases, the implanted device might fail to detect abnormal cardiac events that actually occurred within the patient. Such "false-negatives" can result in a failure to deliver needed therapy. Moreover, because the recording of IEGM data is not triggered unless an abnormal event is detected, false-negatives prevent important IEGM data from being properly recorded and then sent to the external programmer for clinician review. As such, the clinician might be unaware of that certain abnormal events are occurring within the patient.

Accordingly, it is highly desirable to provide techniques for reducing or eliminating the false-positive detection of events of interest, particularly abnormal events, to prevent delivery of inappropriate therapy and to prevent recordation of unneeded IEGM data. It is also highly desirable to provide techniques for reducing or eliminating false-negatives to better ensure proper delivery of therapy and to ensure proper recordation of important IEGM data. It is to these ends that aspects of the invention are generally directed.

SUMMARY OF THE INVENTION

In an exemplary embodiment, a method is provided for use with an implantable medical device such as a pacemaker or ICD. An IEGM or other cardiac signal is sensed within a patient in which the device is implanted using a cardiac signal sensing system. Cardiac events of interest are detected within the patient using event detection systems and then portions of the cardiac signal, including portions representative of the events of interest, are recorded in device memory. Subsequently, portions of the recorded cardiac signal are retrieved and analyzed during an off-line analysis to identify false detections of events of interest. In response to false detections, the cardiac signal sensing system and/or the event detection systems of the device are selectively adjusted or reprogrammed to reduce or eliminate any further false detections of events of interest. Typically, the events of interest are abnormal cardiac events, such as arrhythmias, PACs, PVCs, PMTs, etc., and the device operates to identify false-positive detections of such events during off-line analysis. However, in at least some examples, the device also records apparently normal events for off-line analysis so as to detect false-negatives therein or to redefine what constitutes "normal" cardiac events.

In one embodiment, the implantable device performs an off-line analysis of recorded IEGM data to detect false-positives and false-negatives, then selectively adjusts the sensitivity by which cardiac signals are detected by the cardiac signal sensing system and/or selectively adjusts the parameters by which abnormal cardiac events are detected so as to prevent further false detections of abnormal events. In this regard, at least some false detections of abnormal events are due to improperly set sensitivity values, which results in improper detection of events within the IEGM such as P-waves and R-waves. For example, if the sensitivity is set too high, far-field events can be erroneously detected within a given IEGM channel, triggering false-positive detection of arrhythmias, PACs, PVCs, and the like. If the sensitivity is set too low, near-field events can be missed within the IEGM, resulting in failure to properly detect actual arrhythmias, PACs, PVCs, and the like, i.e. false-negatives occur. By selectively adjusting or reprogramming device sensitivity based on the off-line analysis of recorded IEGM data, false detections due to sensitivity problems can be reduced and, in some cases, completely eliminated. Also, once any false-positive detections have been identified, the corresponding IEGM data can be erased from memory, thereby freeing memory resources for recording data that is more useful.

Other false detections arise due to improperly set detection values employed by the various abnormal event detection components of the implantable device, such as PAC detectors, PVC detectors, arrhythmia detectors, etc. In particular, predetermined ranges of parameter values provided to distinguish normal cardiac events from abnormal cardiac events may be set too wide or too narrow, resulting in false-positives or false-negatives. By selectively adjusting the parameters that define these ranges based on the off-line analysis of the recorded IEGM data, false detections due to range problems or the like can be reduced and, in some cases, completely eliminated. Again, once any false-positive detections have been identified, the corresponding IEGM data can be erased from memory.

Depending upon the implementation, the off-line analysis can be performed by the implantable device itself during periods of time when the device can safely devote processor resources to the analysis, such as while the patient is asleep or inactive and the heart rate is relatively low and stable. In other implementations, the off-line analysis is performed by an external device, such as by a device programmer or a bedside monitor, using IEGM data transmitted from the device. Based on the results of the off-line analysis, the external device then transmits suitable reprogramming commands to the implanted device to reprogram the device to address any false detection problems. When using a device programmer, the IEGM data can be displayed for clinician review, thereby allowing the clinician to confirm the identification of any false detections made by the external system and to also confirm any reprogramming commands recommended by the external device. In the following, it is assumed that the implantable device performs the off-line analysis but it should be understood that the analysis could instead by performed by external devices or systems, including remote systems or distributed processing systems.

Within the device-based implementation, to detect false-positives, the implantable device examines IEGM data previously recorded during abnormal events, including any pre-trigger or post-trigger data. To detect false-negatives, the device examines other portions of recorded IEGM data, such as any IEGM data automatically recorded by the device even in the absence of abnormal events. As noted above, implantable devices can be programmed to continuously detect and record a portion of recent IEGM data in a temporary buffer to accommodate the recordation of pre-trigger data. Such IEGM data can be examined by the device during the off-line analysis to detect false-negatives. In some cases, false-negatives might also be found within IEGM data initially stored in response to detected abnormal events.

Insofar as the analysis of IEGM data is concerned, the implantable device can employ off-line abnormal event detection systems that have greater detection specificity than the "real-time" detection systems ordinarily used by the device during routine processing to detect abnormal cardiac events. By exploiting greater detection specificity during the off-line analysis, the device can distinguish false-positive events from true events and also identify false-negatives that might have been overlooked by the real-time detection systems. As one example, to detect atrial arrhythmias in real-time, the device might simply compare the atrial rate of the patient against one or more thresholds indicative of atrial tachyarrhythmias. The off-line analysis system might instead employ a more sophisticated morphological analysis of the atrial IEGM data to distinguish true atrial tachyarrhythmias from fast sinus rhythms. Typically, the off-line analysis procedures are more processor-intensive than the device is capable of performing in real-time and hence are only employed at times when the device can safely devote the additional processor resources to perform the more sophisticated analysis, such as while the patient is generally inactive. For example, if the device incorporates a multitasking operating system, then a fraction of the operating duty cycle may be allocated to "off-line" processing and the percentage of time allotted may be fixed or variable based on this "generally inactive" determination. The generation of new parameter values based on analysis of IEGM data by the off-line system can be referred to as a "production"-based approached, as it serves to produce a new set of parameter/sensitivity values.

Alternatively, rather than using a more sophisticated off-line system that provides greater detection specificity, the device uses the same basic detection procedures employed in real-time but varies the ranges of detection/sensitivity parameters while repeatedly re-applying the recorded IEGM data to the thereby reveal false-negatives or false-positives. In one particular example, the recorded IEGM data is repeatedly reapplied to the detection systems while various detection/sensitivity parameters are varied throughout a range of values until optimized values are found that eliminate all or most false detections. Then, the actual real-time detection system is reprogrammed to use the optimized values. The generation of new parameter values based on repeated reapplication of IEGM data to the detection systems can be referred to as a "deduction"-based approached, as it serves to deduce a new set of parameter/sensitivity values.

Note that, herein, "off-line" analysis refers to any analysis of cardiac signal data that is delayed relative to real-time and is based on recorded data. This should not to be taken to imply that the implantable device itself is taken off-line, since the device continues to operate within the patient to detect possible abnormal cardiac events and to respond accordingly. Alternatively, off-line analysis can be referred to as "background analysis," "delayed analysis," or "retrospective analysis," or by other suitable terms. Also, herein, "real-time" analysis refers to any substantially non-delayed analysis of cardiac signal data. This should not to be taken to imply that the analysis occurs absolutely simultaneously with events as they occur in the heart of the patient. As can be appreciated, given the limitations of circuits and microprocessors, there can be minor delays between the occurrence of an event in the heart of a patient and its processing by the "real-time" detection components of the implantable device. Nor should this to be taken as implying that the real-time analysis does not itself exploit some form of recorded data, since the real-time components can employ data that is stored, at least temporality, in buffers of the like. More generally, off-line analysis herein refers to any analysis of recorded cardiac signal data that is delayed relative to the real-time analysis by more than a trivial amount of time. Note also that the on-going real-time processing of new cardiac signals does not cease during the off-line analysis. The off-line analysis is a background analysis that is performed contemporaneously with on-going real-time event detection using processing components not required by the real-time event detection components. As part of the off-line analysis, the device can assess how quickly or how early an event was detected. In general, an earlier or quicker detection is likely to be a more accurate or reliable detection than a later or slower detection. As such, this information can be used in assessing false-positives and false-negatives.

Upon detection of a false-positive or a false-negative, the implantable device preferably determines whether the false detection was (1) due to a sensitivity problem, e.g. the sensitivities of the atrial or ventricular channels were not set properly; (2) a detection parameter problem, e.g. the ranges of values used to detect PACs, PVCs, arrhythmias and the like were not set properly; or (3) an inherent problem with the real-time detection systems, e.g. there is no combination of sensitivity values and detection parameter values that serve to substantially eliminate all false detections. If the problem is due to sensitivity, the device adjusts the sensitivities of certain sensing channels to reduce sensitivity so as to, e.g., filter out far-field events that might be triggering false-positives, or to increase the sensitivity so as to, e.g., allow detection of near-field events that might not have been properly detected, resulting in false-negatives. If the problem is due to the detection parameters, the device adjusts selected detection parameters to, e.g., narrow the ranges of the parameters to eliminate false-positives, or to, e.g., expand the ranges of the parameters to eliminate false-negatives. Preferably, any adjustments to sensitivity/detection parameters are limited to relatively small incremental adjustments during each adjustment iteration (i.e. the rate of change of the parameters is restricted) and are also restricted to predetermined overall ranges of acceptable values (i.e. the scope of changes to the parameters is restricted). Also, preferably, a history of prior adjustments is maintained and exploited so as to prevent previous adjustments that may have been ineffective from being repeated.

If the detection issue is due to an inherent problem with the real-time detection system, the implantable device can take various actions based on device programming. The device can generate warning signals to notify the patient and/or clinician that abnormal events are occurring within the patient that are not being properly detected. The clinician then takes appropriate steps to remedy the problem such as by, e.g., adjusting the location of the leads of the device to improve cardiac signal sensing or by adjusting any operating parameters of the device that are beyond the scope of the off-line adjustments the device itself can make. The implantable device can also reset the various detection/sensitivity parameters to default values or to previous sets of programmed values that might yield a better, albeit not perfect, detection of abnormal events. The device can also grade the severity of various abnormal events and block the recording of IEGM data for any series of abnormal events of the same or decreasing severity (i.e. the device inhibits serial triggering of multiple events of the same or decreasing severity.) For example, the device might grade arrhythmias as being more severe than PVCs and PACs and then inhibit the recording of IEGM data due to PVCs and PACs following the recording of IEGM data triggered due to an arrhythmia. Otherwise, IEGM data from arrhythmias might eventually be overwritten by IEGM data from less significant events once the memory of the device becomes full. Still further, the device can adjust the various real-time detection/sensitivity parameters so as to achieve a predetermined degree of bias between false-positive and false-negatives. In this regard, the device might bias the real-time detection components so as to ensure there will be substantially no false-negatives, even if it means that false-positives will occur, or vice versa.

Thus, techniques have been summarized whereby, inter alia, data collection is triggered based on the natural or intrinsic changes in device operation in relation to the patient (based on, e.g., heart rhythm.) This is generally in contrast with "provocative" techniques that change the operation of the device to obtain data for use in reprogramming the device. It should be understood, though, that a device equipped to perform the techniques of the invention might additionally utilize provocative techniques and then exploit data collected from the provocative techniques in combination with any "triggered" data.

System and method implementations of these and other techniques are presented herein.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
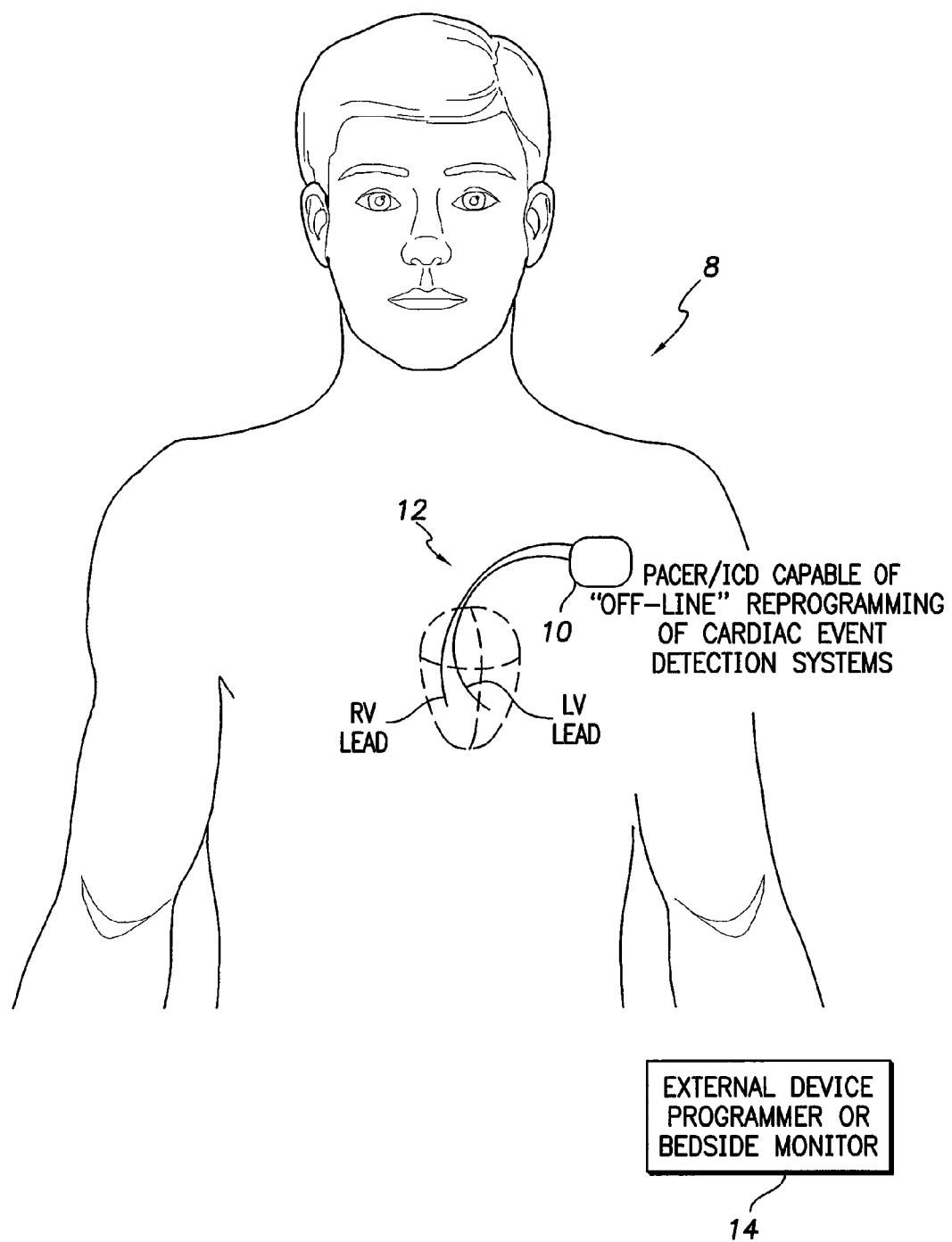
FIG. 1 illustrates pertinent components of an implantable medical system having a pacemaker or ICD equipped to perform an off-line analysis of recorded IEGM data to identify false detections of cardiac events of interest and to then reprogram sensitivity values and/or event detection parameters to address any such false detections.

FIG. 1 illustrates an implantable medical system 8 capable of performing off-line analysis and reprogramming of internal device components/procedures to address false detections of cardiac events of interest, particularly abnormal events.

Medical system 8 includes a pacer/ICD 10 or other cardiac rhythm management device equipped with one or more cardiac sensing/pacing leads 12 implanted within the heart of the patient for use in sensing electrical cardiac signals. (Note that FIG. 1 provides only a stylized representation of exemplary leads. A more complete and accurate illustration of a set of leads is provided in FIG. 14.) The pacer/ICD processes the cardiac signals substantially in real-time using internal components and procedures to detect cardiac events of interest— such as arrhythmias, PACs, PVCs, etc.—and then responds to the events by delivering various appropriate therapies or by performing other suitable actions. These responses may be otherwise conventional. The pacer/ICD also records the cardiac signal data corresponding to the events of interest in internal memory in the form of IEGM data. Later, when processor resources are available, an off-line or background analysis of the recorded IEGM data is performed to identify false detections of events of interest and then selected internal components/procedures of the pacer/ICD are reprogrammed to reduce or eliminate further false detections. This will be described in greater detail below.

In some implementations, the pacer/ICD itself performs the off-line analysis based on the recorded IEGM data stored within its memory system and then automatically reprograms its internal components/procedures to address false detections. In other implementations, the device transmits the recorded IEGM data via telemetry to an external device programmer 14 that performs the off-line analysis. The programmer analyzes the recorded IEGM data to identify false detections of events of interest and then generates suitable programming commands for reprogramming the internal components/procedures of the pacer/ICD to address the false detections. In some implementations, a clinician confirms the programming commands before the commands are transmitted to the pacer/ICD. Note that other external devices might instead be used to perform the off-line analysis, such as bedside monitors, remote monitoring systems, distributed systems, or the like. In at least some embodiments, the external system automatically performs the reprogramming without clinician supervision or confirmation. Note also that the device programmer or bedside monitor can be directly networked with a centralized computing system, such as the HouseCall™ system or the Merlin@home/Merlin.Net systems of St. Jude Medical.

In the following examples, it is assumed that the pacer/ICD performs the off-line analysis. An example where the external programmer performs the analysis is described below with reference to FIG. 13.

Overview of Off-Line Analysis and Reprogramming

Figure 2:
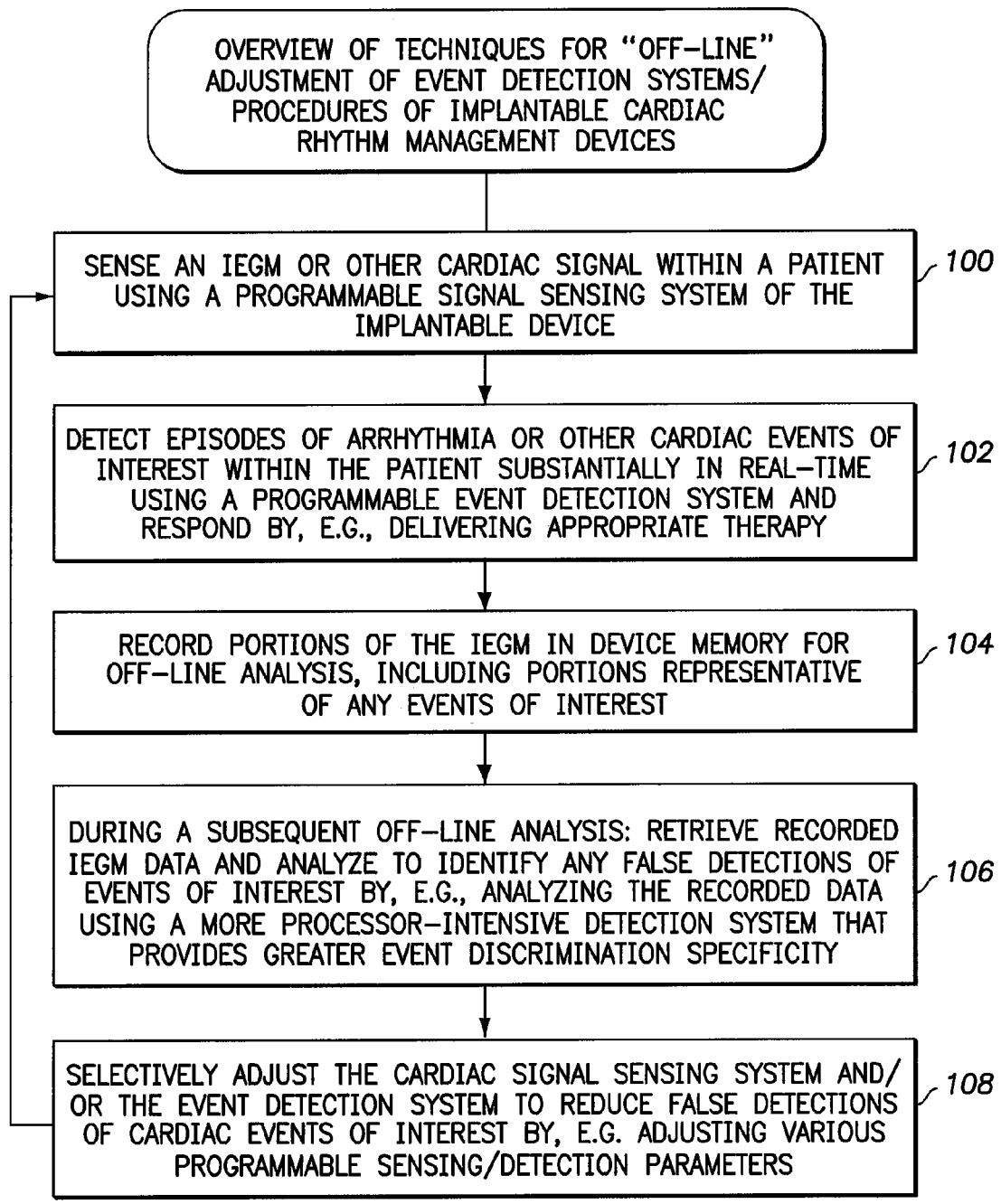
FIG. 2 is a flowchart providing an overview of a technique for the off-line adjustment of sensitivity values and/or event detection parameters, which can be performed by the system of FIG. 1.

FIG. 2 broadly summarizes a general technique for off-line adjustment of abnormal event detection systems/procedures of pacer/ICDs or other implantable cardiac rhythm management devices. Beginning at step 100, the pacer/ICD senses an IEGM or other cardiac signal within the patient using a programmable signal sensing system of the pacer/ICD, which may include various sense amplifiers and the like described in greater detail below with reference to FIG. 15. At step 102, the pacer/ICD detects episodes of arrhythmia or other cardiac events of interest such as PACs, PVCs, PMTs, etc. within the patient substantially in real-time using an on-board programmable event detection system and responds to the events by, e.g., delivering appropriate therapy or by inhibiting or activating various other responses. The techniques by which the pacer/ICD senses cardiac signals and then detects and responds to cardiac events of interest can be otherwise conventional.

At step 104, the pacer/ICD then records portions of the IEGM in device memory for off-line analysis, including IEGM data representative of any events of interest. As already noted, IEGM data can include digitized IEGM signals from various atrial and ventricular sensing channels as well as related data, such as event markers and the like. In one example, both pre-trigger and post-trigger IEGM data is stored using techniques described in the above-cited patent documents of Ferrise et al., and Kroll. At step 106, during a subsequent off-line analysis, the recorded IEGM data is retrieved and analyzed to identify any false detections of events of interest by, e.g., analyzing the recorded IEGM data using a more processor-intensive detection system that provides greater event discrimination specificity. For example, to identify false detections of atrial tachyarrhythmias, the off-line analysis might exploit a more sophisticated morphological analysis, whereas the real-time detection of atrial tachyarrhythmias might be based solely on the atrial rate as compared to various thresholds. Various exemplary off-line analysis techniques will be described in detail below. Note that the on-going real-time processing of new cardiac signals at steps 100 and 102 does not cease during the off-line analysis of step 106. The off-line analysis is a background analysis that is performed contemporaneously with on-going real-time event detection using processing components not required by the real-time event detection components.

At step 108, the cardiac signal sensing systems and/or the real-time event detection systems of the pacer/ICD are selectively adjusted in an effort to reduce or eliminate false detections of cardiac events of interest by, e.g., adjusting or reprogramming various programmable sensing/detection parameters. Various exemplary off-line reprogramming techniques will be described in detail below. In some cases, the adjustments will be sufficient to substantially eliminate all false detections. In other cases, perhaps due to inherent limitations in the on-board signal sensing systems and/or the real-time abnormal event detection systems, the reprogramming will only be able to reduce the number of false-detections or, in some cases, the device might only be able to adjust the bias between false-positive and false-negatives. These and other responses will be described below.

Steps 100-108 may be repeated in a loop, as shown, so as to iteratively or adaptively reprogram the real-time sensing and detection systems of the pacer/ICD to allow these systems to adapt over time to changing conditions within the patient, as might be caused by the progression of heart disease or by the administration of medications that affect the cardiac signals being sensed. In some implementations, all of the steps are performed by the pacer/ICD. In other implementations, at least some of these steps, such as steps 106 and 108, are performed by an external system in communication with the implantable device. An example exploiting off-line processing by an external system will be described below with reference to FIG. 13.

Thus, FIG. 2 summarizes a technique whereby data collection is triggered (at step 104) based on the natural or intrinsic changes in device operation in relation to the patient (based on, e.g., heart rhythm.) This is generally in contrast with "provocative" techniques that change the operation of the device to obtain data. For provocative techniques, see, for example, U.S. Pat. Nos. 7,558,627; 5,891,176; and 5,487,752. These patents described, inter alia, provocative procedures that a device invokes whereby the device changes its operation to perform a test—with the results of said test then being used to "reprogram" the device—so as to adapt device operation based on the test results. It should be understood, though, that a device equipped to perform the "non-provocative" technique of FIG. 2 might additionally utilize provocative techniques and/or might exploit data collected from provocative techniques in combination with the non-provocative "triggered" data obtained at step 104.

Pacer/ICD-Based Off-Line Analysis/Reprogramming Examples

Figure 3:
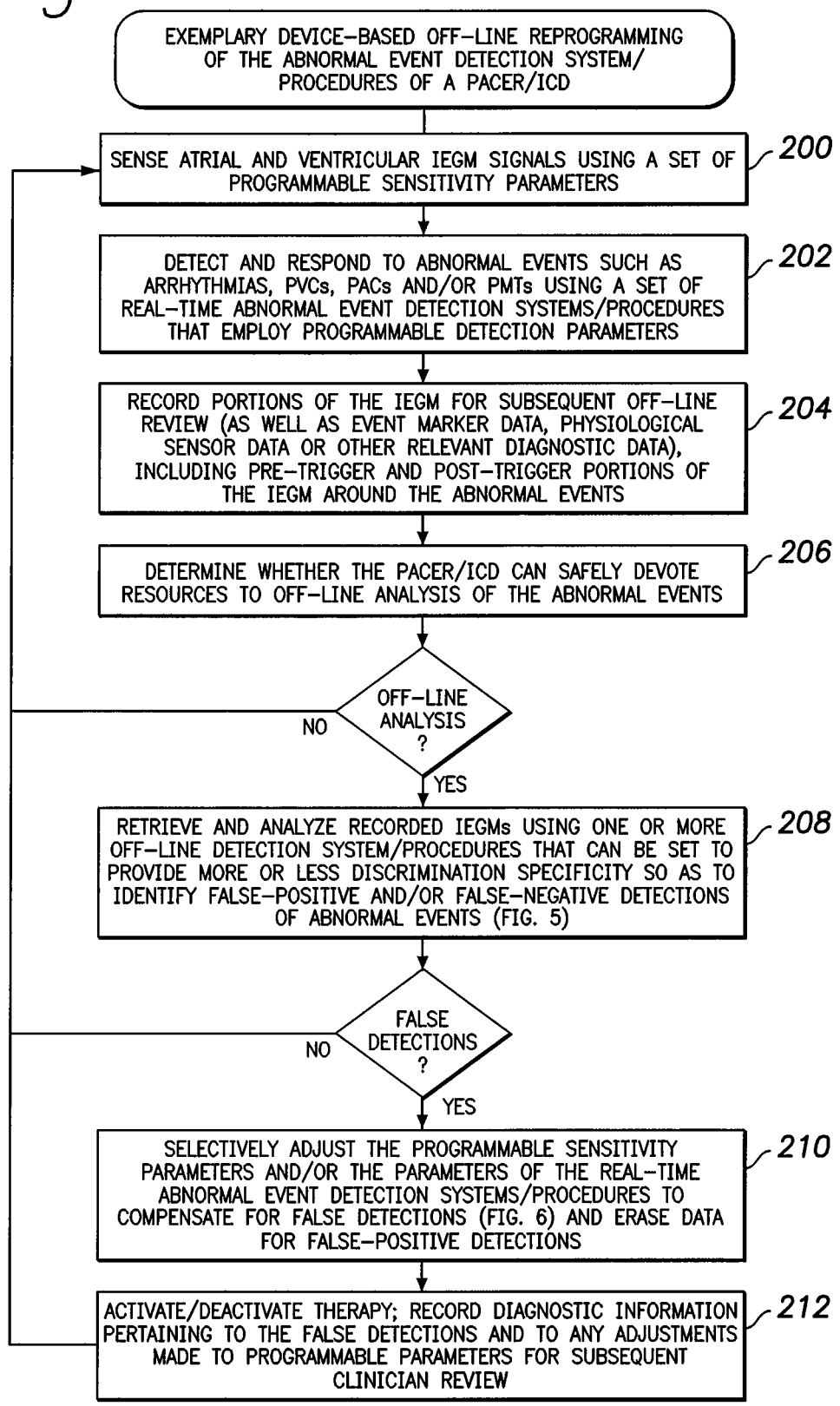
FIG. 3 illustrates an illustrative implementation of the general technique of FIG. 2, primarily directed to detecting abnormal events.

FIG. 3 illustrates an exemplary device-based technique for off-line adjustment of event detection systems/procedures of a pacer/ICD, particularly abnormal event detection systems and procedures. Beginning at step 200, the pacer/ICD senses atrial and ventricular IEGM signals using a set of programmable sensitivity parameters. Typically, each sensing channel has at least one adjustable value for use in specify the sensitivity by which cardiac events, such as P-waves, R-waves and T-waves, are detected on the channel. State-of-the-art devices accommodate at least a few different sensing channels and, in some cases, many separate channels.

At step 202, the pacer/ICD detects abnormal cardiac events such as arrhythmias, PVCs, PACs and/or PMTs using a set of real-time abnormal event detection systems/procedures that employ programmable detection parameters. Other specific abnormal events that might be detected and used to trigger the recordation of IEGM data include: loss of capture (LOC); atrial tachycardia (AT); atrial fibrillation (AF); ventricular tachycardia (VT); ventricular fibrillation (VF); and the like. If the pacer/ICD is equipped to perform AMS, an AMS event can also be regarded as an abnormal cardiac event. With AMS, the pacer/ICD reverts from a tracking mode such as a VDD or DDD mode to a nontracking mode such as VVI or DDI mode upon detection of certain conditions, particularly AT/AF. Still other abnormal cardiac events may be detected based on the capabilities of the device. For example, the pacer/ICD might be capable of detecting, e.g., atrial flutter, supraventricular tachycardia (SVT), sinus tachycardia (ST), atrioventricular re-entrant tachycardia (AVRT), atrioventricular nodal re-entrant tachycardia (AVNRT), idiopathic RV tachycardia, idiopathic LV tachycardia, and/or atrial or ventricular bigeminy, trigeminy, etc. In general, any abnormal cardiac event (or combination of events) detectable by the pacer/ICD within the electrical cardiac signals of the heart can be employed as a trigger to trigger the recording of IEGM data, whether the event constitutes an arrhythmia or otherwise.

Also at step 202, the pacer/ICD responds to the abnormal cardiac events by, e.g., initiating any therapies appropriate to the detected abnormal event, such as by delivering therapy in response to arrhythmias.

At step 204, the pacer/ICD then records portions of the IEGM for subsequent off-line review (as well as event marker data, physiological sensor data or other relevant diagnostic data), including pre-trigger and post-trigger portions of the IEGM around the detected abnormal events. Insofar as physiological sensor data is concerned, if the device is equipped to sense various physiological parameters such as arterial blood pressure, left atrial pressure (LAP), etc., portions of these physiological signals can be digitized and stored along with the IEGM data for subsequent review or analysis. In some cases, these physiological signals might be helpful in distinguishing false detections from true detections of abnormal cardiac events.

At step 206, the pacer/ICD determines whether it can safely devote resources to off-line analysis of the abnormal events. That is, the pacer/ICD determines whether it can devote sufficient processor resources to performing the analysis while still properly monitoring the real-time cardiac signals of the patient and responding as needed. This determination may be made by based on the current processing load of the microprocessor or the device, in combination with activity sensors, circadian sensors, or the like. In some cases, the off-line analysis will be performed while the patient is asleep or otherwise inactive, as the patient's heart rate might be more stable at that time, with few or no on-going abnormal events. For example, if the device incorporates a multitasking operating system, then a fraction of the operating duty cycle may be allocated to "off-line" processing and the percentage of time allotted may be fixed or variable based on this "generally inactive" determination. In some cases, the device might be programmed to simply perform the off-line analysis periodically.

Assuming off-line analysis is appropriate, then, at step 208, the pacer/ICD retrieves and analyzes the recorded IEGMs using one or more off-line detection system/procedures that can be set to provide more or less discrimination specificity than the real-time system so as to identify false-positive and/or false-negative detections of abnormal events. Exemplary techniques for detecting false-positives and false-negatives are described below with reference to FIG. 4. Note that the on-going real-time processing of patient cardiac signals at steps 200 and 202 does not cease during the off-line analysis. As already noted, the off-line analysis is a background process that is performed contemporaneously with on-going real-time event detection.

If one or more false detections have been identified, then, at step 210, the pacer/ICD selectively adjusts or reprograms the programmable sensitivity parameters (used at step 200) and/or the parameters of the real-time abnormal event detection systems/procedures (used at step 202) so as to compensate for false detections. Various automatic adjustment techniques are shown in FIGS. 4-12. At step 210, the pacer/ICD can also delete or erase (or mark for erasure) those portions of device memory that contain IEGM data recorded in response to false-positive detections. This frees memory for recording IEGM data from true abnormal events.

At step 212, in the event that the pacer/ICD is delivering any on-going therapy (activated at step 202) that had been triggered by an event subsequently deemed to be a false-positive, the pacer/ICD deactivates that therapy. If false-negatives have been detected, particularly recent ones, the device might activate therapies. Also at step 212, the pacer/ICD can record diagnostic information pertaining to the false detections and to any adjustments made to programmable parameters for subsequent clinician review. Such diagnostic data might specify the data and time of the original event that was subsequently deemed to be a false event during the off-line analysis, and whether the event was a false-positive or a false-negative.

As with the steps of FIG. 2, the steps of FIG. 3 may be repeated in a loop, as shown, so as to iteratively or adaptively reprogram the real-time sensing and detection systems of the pacer/ICD to allow these systems to adapt over time to changing conditions within the patient.

Figure 4:
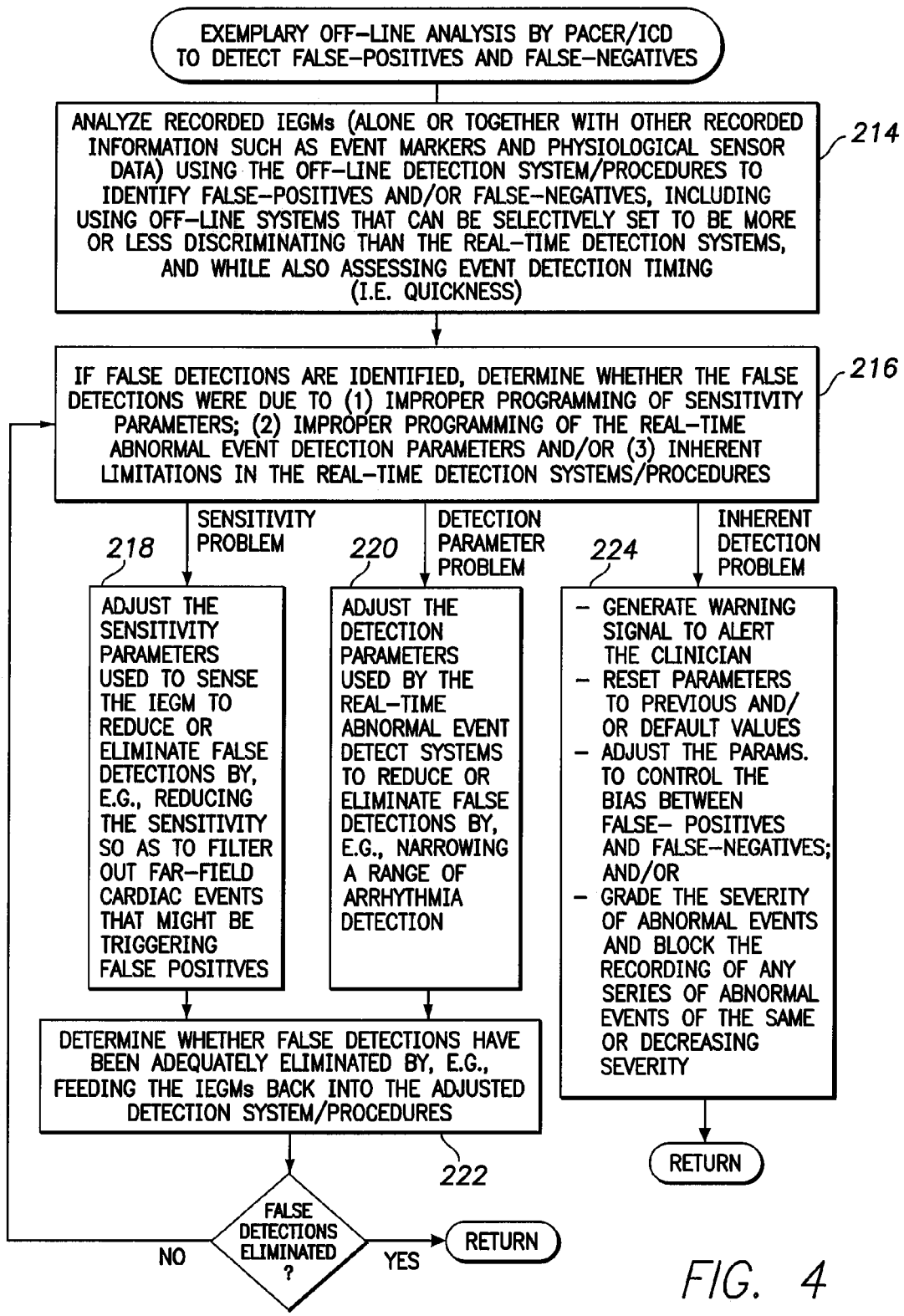
FIG. 4 illustrates exemplary techniques for use with the implementation of FIG. 3 for detecting and distinguishing false-positives and false-negatives.

Turning now to FIG. 4, an exemplary off-line technique for detecting and responding to false detections will be described. These off-line analysis steps run in the background while real-time event detection is on-going by the device. At step 214, the pacer/ICD analyzes the IEGMs recorded during previously-detected abnormal events and any other IEGM data that has been recorded (alone or together with other recorded information such as event markers and physiological sensor data) using the off-line detection system/procedures to detect false-positives and/or false-negatives. To detect false-positives, the pacer/ICD examines IEGM data previously recorded during abnormal events, including any pre-trigger or post-trigger data. To detect false-negatives, the pacer/ICD examines other portions of recorded IEGM data, such as any IEGM data automatically recorded by the device in temporary buffers. As noted above, pacer/ICD can be programmed to continuously detect and record a portion of recent IEGM data in a circular queue to accommodate the recordation of pre-trigger data. Such IEGM data can be examined by the pacer/ICD during the off-line analysis to detect false-negatives. In some cases, false-negatives might also be found within IEGM data stored in response to abnormal events. That is, false-negatives can sometimes be identified within portions of IEGM data that had been originally recorded in response to abnormal events (which might have been false-positive events or properly detected events.)

The off-line analysis of step 214 can be achieved by exploiting off-line detection systems that can be set to be more or less discriminating than the real-time detection systems (employed at step 202 of FIG. 3.) As noted, one example of an off-line system that is generally more discriminating than the real-time systems are detection systems that employ morphological analysis of the IEGM. In other cases, the pacer/ICD uses the same basic detection procedures that are employed at step 202 of FIG. 3 for real-time detection but varies the sensitivity/detection parameters of the off-line versions of the procedures to reveal false-positives. As one particular example, false-positives can sometimes occur due to far-field sensing of ventricular events on an atrial sensing channel. These false-positives can be exposed by adjusting atrial sensitivity values to eliminate the far-field R-waves. As another example, false-positives can sometimes occur due to T-wave oversensing on a ventricular sensing channel. These false-positives can be exposed by adjusting ventricular sensitivity values to eliminate the T-wave oversensing.

One example of an off-line system that is generally less discriminating than the real-time systems are detection systems that employ a comparatively wider range of detection parameters. By employing a wider range of values (such as a wider range of atrial rates), more cardiac events thereby fall into the range and are identified as abnormal cardiac events. In other cases, the pacer/ICD uses the same basic detection procedures that are employed at step 202 of FIG. 3 for real-time detection but varies the sensitivity/detection parameters of the off-line versions of the procedures to reveal false-negatives. As one particular example, false-negatives can sometimes occur due to undersensing of near-field events on sensing channels. These false-negatives can be exposed by adjusting sensitivity values to eliminate the undersensing.

Depending upon the particular abnormal event, and the capabilities of the device, the pacer/ICD can also use physiological sensor data to confirm or establish the false detection. In this regard, some abnormal events are expected to have certain affects on physiological parameters, such as by causing a reduction in blood pressure or LAP. As such, this data, if it is available, can be analyzed in combination with the IEGM data to identify false detections.

Also, at step 214, the device can assess the relative timing of false detections. That is, as part of the off-line analysis, the device can assess how quickly or how early an abnormal event was detected. In general, an earlier or quicker detection is likely to be a more accurate or reliable detection than a later or slower detection. As such, this information can be used in assessing false-positives and false-negatives. As one example, the longer it takes the device to classify a given cardiac rhythm as being "abnormal," the less likely the rhythm is truly abnormal (that is, the more likely the detection of the abnormal rhythm is a false-positive.)

At step 216, if one or more false detections are identified, the pacer/ICD determines whether the false detections were due to (1) improper programming of sensitivity parameters; (2) improper programming of the real-time abnormal event detection parameters and/or (3) inherent limitations in the real-time detection systems/procedures. Typically, the determination depends on the particular cardiac event that triggered the false detection, whether it was a false-negative or a false-positive, and the manner by which it was detected. For example, if changes to sensitivity values were needed to expose a false-positive or false-negative, then the false detection was likely due to improper programming of sensitivity parameters. If changes to detection parameter values were needed to expose false-positives or false-negatives, then the false detections were likely due to improper programming of the detection parameters. The special case where inherent limitations exist in the real-time detection systems/procedures (i.e. case (3)) will be discussed below.

If the false detection was due to a sensitivity problem, then, at step 218, the pacer/ICD adjusts the sensitivity parameters used to sense the IEGM in real-time to reduce or eliminate further false detections by, e.g., reducing the sensitivity so as to filter out far-field cardiac events that might be triggering false positives or increasing the sensitivity to reduce undersensing. The selective adjustment of sensitivity values is discussed further below with reference to FIG. 5. If the false detection was due to a detection parameter problem, then, at step 220, the pacer/ICD adjusts the detection parameters used by the real-time abnormal event detect systems to reduce or eliminate the false detections by, e.g., narrowing a range of event detection in response to a false-positive or widening the range in response to a false-negative. As one particular example, AT might be detected in real-time based on the atrial rate exceeding an AT rate threshold. This threshold might be set too low, thereby causing fast sinus rhythms to be misidentified as AT. If so, the AT threshold can be increased to thereby effectively narrow the range in which AT is detected so as to reduce false-positives of AT. The selective adjustment of detection parameters is discussed further below with reference to FIG. 6.

After adjusting the sensitivity and/or detection parameters, the pacer/ICD, at step 222, determines whether the false detections have been adequately eliminated by, e.g., feeding the IEGMs back into an adjusted version of the real-time detection system/procedures. That is, the same procedures used during real-time to detect cardiac events can be emulated by the off-line system but programmed to employ the new values/parameters. The recorded IEGMs are then fed into the emulated real-time procedure to determine if the procedure now properly detects abnormal cardiac events with no significant occurrences of false-positives or false-negatives. If so, then the false detections have been adequately eliminated. If not, further adjustments are made by repeating steps 216-222. In one example, the recorded IEGMs are repeatedly fed into an emulated real-time detection procedure (that emulates the detection procedure of step 202 of FIG. 3), along with indications of true and false abnormal cardiac events, so as adaptively train the detection procedure to properly detect actual abnormal events while rejecting false events. Adaptive retraining of a detection system is discussed further below with reference to FIG. 7.

Once a set of sensitivity values and detection parameters have been identified using the off-line systems that serve to substantially eliminate false detections, processing returns to step 210 of FIG. 3 where the new set of values and parameters are then used to reprogram the actual real-time sensing and detection systems of steps 200 and 202 so as to reduce or eliminate further false detections.

If, at step 216 of FIG. 4, no set of sensitivity values and/or detection parameters serve to eliminate substantially all false detections, then there might be an inherent problem or limitation in the detection procedure. Hence, if repeated iterations of steps 216-222 through all ranges of acceptable values/parameters fail to identify a suitable set of values/parameters, an inherent detection problem is thereby identified and processing proceeds to step 224

At step 224, the pacer/ICD can take various actions, based on device programming. The device can generate warning signals to notify the patient and/or clinician that abnormal events are occurring within the patient that are not being properly detected. Warnings can be generated using an internal warning device within the pacer/ICD (such as a vibrating device or a voltage "tickle" device) or via a beside monitor or a personal advisory module (PAM). The patient then notifies the clinician or, in some cases, the clinician is automatically notified via networked systems. The clinician then takes appropriate steps to remedy the detection problem such as by, e.g., adjusting the location of the leads of the pacer/ICD to improve cardiac signal sensing or by adjusting any operating parameters of the pacer/ICD that are beyond the scope of the off-line adjustments the pacer/ICD itself can make within steps 218 and 220.

At step 224, the pacer/ICD can also reset the various detection/sensitivity parameters to default values or to previous sets of programmed values that might yield a better, albeit not perfect, detection of abnormal events. The pacer/ICD can also grade the severity of various abnormal events and inhibit the recording of IEGM data for any series of abnormal events of the same or decreasing severity (i.e. the pacer/ICD inhibits serial triggering of multiple events of the same or decreasing severity.) For example, the pacer/ICD might grade arrhythmias as being more severe than PVCs and PACs and then inhibit the recording of IEGM data due to PVCs and PACs following the recording of IEGM data triggered due to an arrhythmia. Otherwise, IEGM data from arrhythmias might be eventually overwritten by IEGM data from less significant events, once the memory of the device becomes full. Still further, the pacer/ICD can adjust the various real-time detection/sensitivity parameters so as to achieve a predetermined degree of bias between false-positive and false-negatives. In this regard, the device might bias the real-time detection components so as to ensure there will be substantially no false-negatives, even if it means that false-positives will occur, or vice versa. In another example, the device might set the bias such as false-positives and false-negatives are equally likely.

Figure 5:
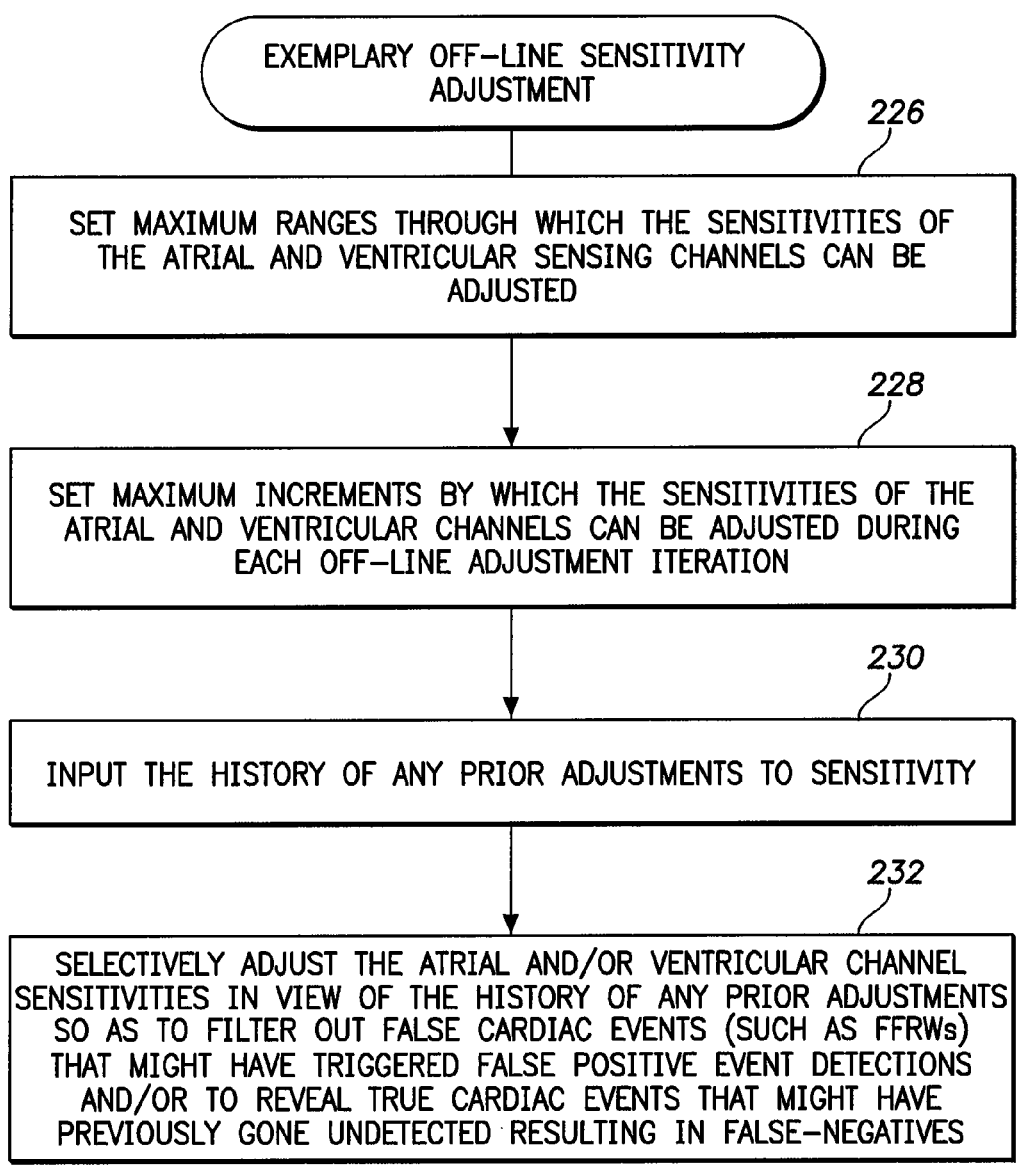
FIG. 5 illustrates exemplary techniques for use with the embodiment of FIG. 4 for the off-line adjustment/reprogramming of sensitivity.
Figure 6:
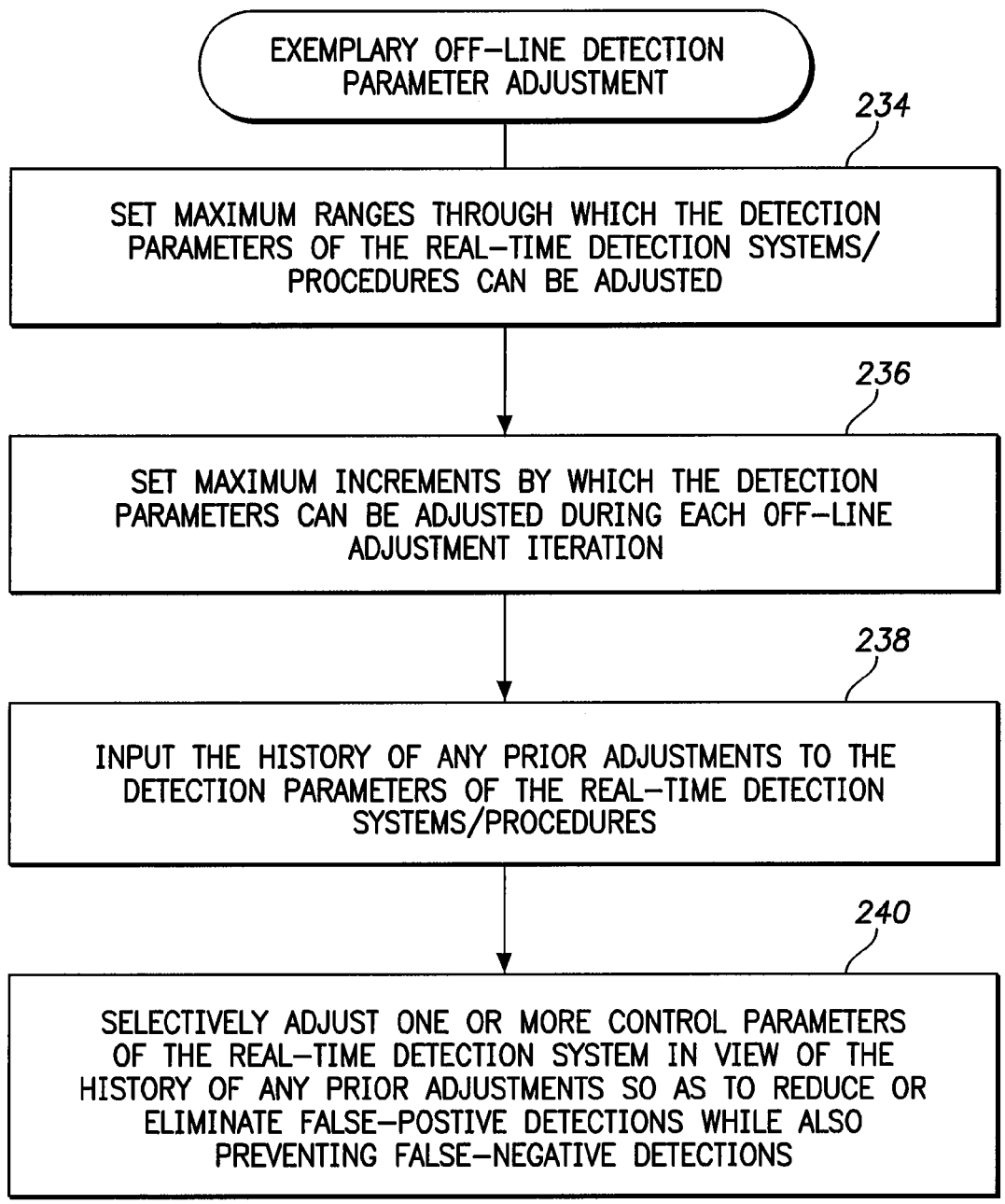
FIG. 6 illustrates exemplary techniques for use with the embodiment of FIG. 4 for the off-line adjustment/reprogramming of abnormal event detection parameters.
Figure 7:
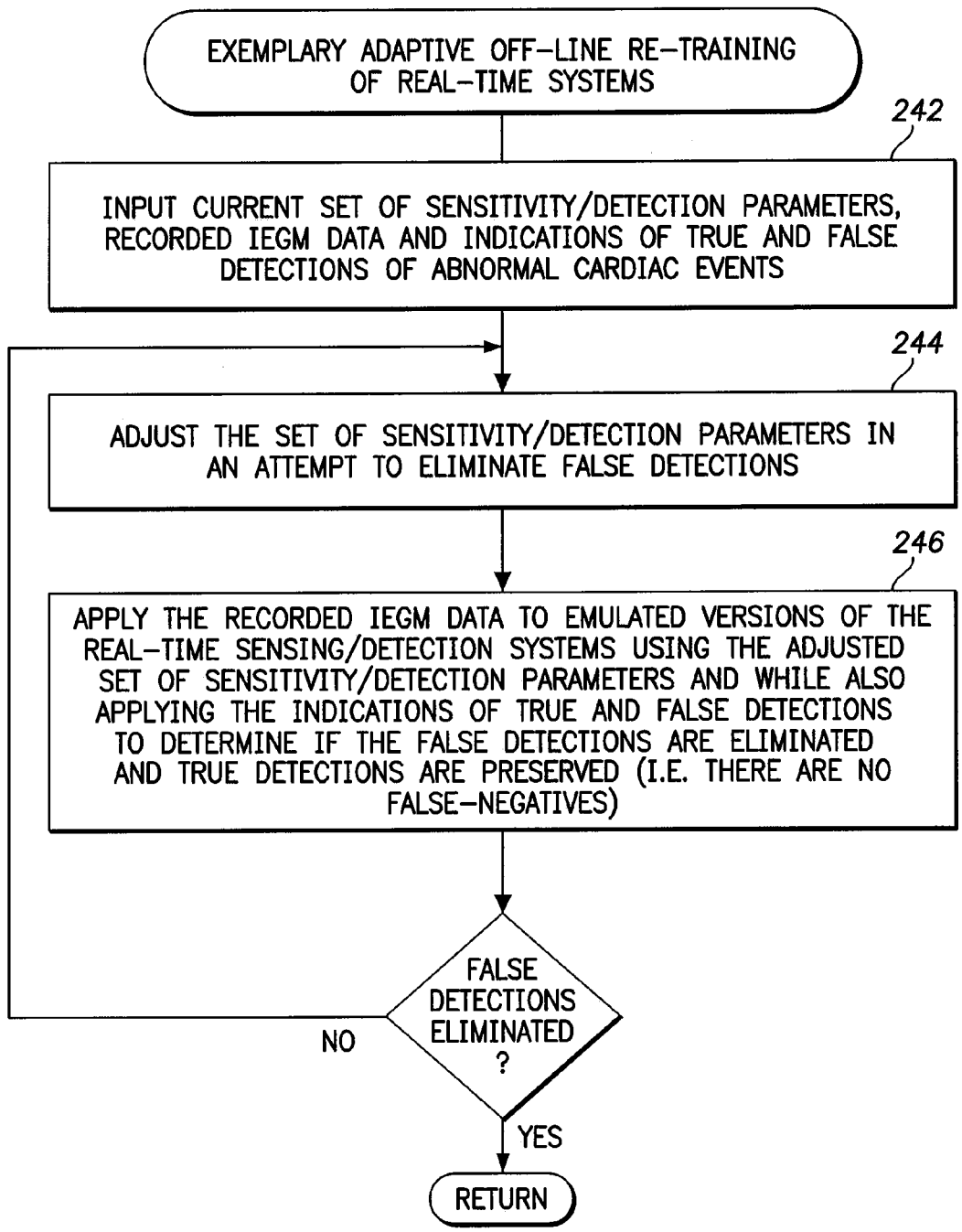
FIG. 7 illustrates exemplary techniques for use with the embodiment of FIG. 4 for adaptive and iterative off-line adjustment of sensitivity/detection parameters.

Turning now to FIGS. 5-7, various exemplary sensitivity value and detection parameters adjustment or retraining techniques will be described for use during an off-line analysis and reprogramming session.

FIG. 5 illustrates exemplary techniques for the off-line adjustment of sensitivity that may be performed in connection with the technique of FIG. 4, particular step 218. At step 226 of FIG. 5, the pacer/ICD sets maximum ranges within which the sensitivities of the atrial and ventricular sensing channels can be adjusted. That is, the "scope" or total range through which the parameters can be adjusted is restricted to a predetermined or programmable range. At step 228, the pacer/ICD set maximum increments by which the sensitivities of the atrial and ventricular channels can be adjusted during each off-line adjustment iteration. That is, the "rate" at which the parameters are adjusted is restricted to a predetermined or programmable adjustment rate. At step 230, the pacer/ICD inputs the history of any prior adjustments to sensitivity values. This may include a list of prior adjustments made to the sensitivity values and the efficacy those adjustments had in eliminating false detections. By taking the history into account, redundant adjustments can be avoided. At step 232, the pacer/ICD then selectively adjusts the atrial and/or ventricular channel sensitivities in view of the history of any prior adjustments so as to filter out false cardiac events (such as FFRWs) that might have triggered false positive event detections and/or to reveal true cardiac events that might have previously gone undetected resulting in false-negatives. Depending upon the capabilities of the device, step 232 may exploit adaptive re-training. See FIG. 7 for an example of adaptive re-training.

FIG. 6 illustrates exemplary techniques for the off-line adjustment of detection parameters that may be performed in connection with the technique of FIG. 4, particularly step 220. At step 234 of FIG. 6, the pacer/ICD sets maximum ranges through which various detection parameters can be adjusted, such as the ranges of atrial or ventricular rates used to detect certain arrhythmias. At step 236, the pacer/ICD sets the maximum increment by which the detection parameters can be adjusted during each off-line adjustment iteration. At step 238, the pacer/ICD inputs the history of any prior adjustments to detection parameters. At step 240, the pacer/ICD then selectively adjusts the detection parameters in view of the history of any prior adjustments so as to reduce or eliminate false-positive detections while also preventing false-negative detections. Depending upon the capabilities of the device, step 240 may exploit adaptive re-training as shown in FIG. 7.

FIG. 7 illustrates an example of adaptive re-training of sensitivity/detection parameters during off-line analysis. At step 242, the off-line analysis system of the pacer/ICD inputs the current set of sensitivity/detection parameters, previously recorded IEGM data, and indications of true and false detections of abnormal cardiac events already detected within the IEGM data (such as those detected during step 214 of FIG. 4.) At step 244, the pacer/ICD adjusts the sensitivity/detection parameters in an attempt to eliminate false detections, such as by making incremental adjustments to the values. At step 246, the pacer/ICD then applies the recorded IEGM data to emulated versions of the real-time sensing/detection systems of the device using the adjusted sensitivity/detection parameters and while also applying the indications of true and false detections to determine if the false detections are eliminated and true detections are preserved. For example, linear discriminators or other pattern classifiers may be exploited that can be adaptively trained. Techniques for training linear discriminators or other pattern classifiers are described, e.g., in U.S. patent application Ser. No. 11/558,787, filed Nov. 10, 2006, now U.S. Pat. No. 8,262,578, of Bharmi et al., entitled "System and Method for Detecting Physiologic States based on Intracardiac Electrogram Signals while Distinguishing Cardiac Rhythm Types."

If false-detections are substantially eliminated, then the off-line analysis is complete. The set of sensitivity/detection parameters that served to eliminate the false detections using the emulated real-time sensing/detection systems are then used to re-program the actual real-time sensing/detection systems for use in detecting further abnormal events within the patient. If false-detections are not yet substantially eliminated, then processing returns to step 244 for further adjustments to the parameters. This process continues until a set of sensitivity/detection parameters are found that successfully eliminate false detections. If no set of parameters are found that substantially eliminate false detections, then an inherent detection problem is thereby detected and suitable steps are taken, as already explained in connection with step 224 of FIG. 4.

Alternative Device-Based Implementations

Turning now to FIGS. 8-12, various alternative techniques for performing off-line device reprogramming of the pacer/ICD of FIG. 1 will now be described, wherein a state-based representation of the operation of the pacer/ICD is employed.

Figure 8:
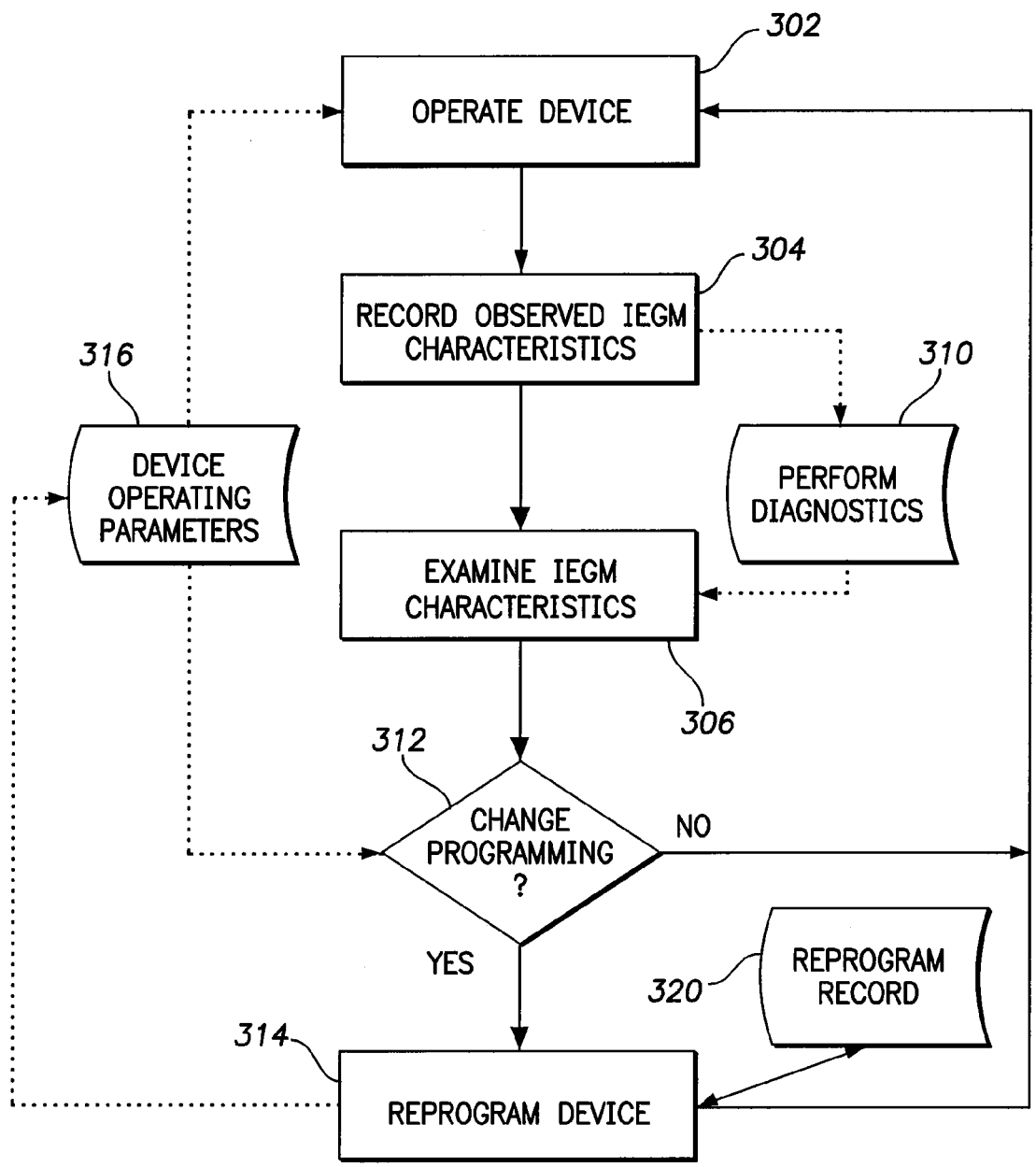
FIG. 8 is a high level overview of an alternative method for off-line reprogramming of the implantable device of FIG. 1 to improve device performance.

FIG. 8 shows a general overview of the operation of device 10 in this alternative implementation. State 302 indicates normal, ongoing operation of device 10 under present programming and with the presently set operating parameters. The parameters can include parameters programmed at implantation and also parameters determined by device 10 after ongoing operation. The parameters can include patient age, an average rate, a maximum rate, a resting rate, a rate distribution (e.g. % operation at different rates or rate ranges), % paced vs. % sensed, A-V delay, etc. The parameters can also include programmed or enabled therapies. It should be understood that for production efficiency and convenience and cost concerns, device 10 may include multiple therapies and functions that are available, however are selectively enabled or set by a clinician to adapt a generic device to the specific needs of a particular patient. It should also be understood that the needs of a patient can change over time, thus possibly indicating a change in device programming.

State 304 follows from state 302 and includes a recording of observed IEGM characteristics. These rate characteristics can include both directly measured characteristics of the IEGM such as the amplitude of a sensed ventricular contraction as well as determined or calculated characteristics such as the % of paced events vs. the % of sensed or intrinsic events.

State 306 follows from the recording of state 304 and comprises an examination of the observed IEGM characteristics. The examination of state 306 can include a comparison among different observed characteristics, an examination of an apparent change of a particular characteristic over time, an observation of a new unexpected type of characteristic, and/or a confirmation of observation of expected characteristics. The goal of the examination of state 306 is to detect false events.

Proceeding from the examination of state 306 is a decision state 312 wherein the device decides whether a change in the programming is indicated. A "NO" decision indicates an optimal match between device 10 operation and patient need. A "YES" decision results when the examination of state 306 indicates that some sort of adjustment to the device may be indicated to improve performance thereof. A YES decision in state 312 will typically result in a change in the programming under a state 314 that will also typically change device 10 operating parameters indicated as block 316.

The reprogramming that occurs in state 314 can include changing the sensitivity of device 10 to attempt to detect events that might be missed, changing a minimum or maximum rate to induce the device to take greater control of heart function, to enable or disable particular therapy regimens, and/or to change the criteria under which the device determines that a particular event is occurring. It should be understood that a wide variety of aspects of device operation may be changed or considered in various embodiments and that the specific examples described herein are exemplary.

Also proceeding in parallel are states 310 wherein diagnostics of the device operation are performed as well as a recording in state 320 of device reprogramming. States 310 and 320 provide a clinician (during a subsequent review) with information relating to device performance. In particular, states 310 and 320 can inform the clinician of possible changes in the device operation since implantation. This can provide valuable information about potential changes in the patient's condition as well as refinements in what optimal device 10 operational parameters the device itself has determined. It should be understood that, in certain embodiments, a clinician can override certain reprogramming changes and/or set limits beyond which the device may not self-change its operation without confirmation of the clinician.

Figure 9:
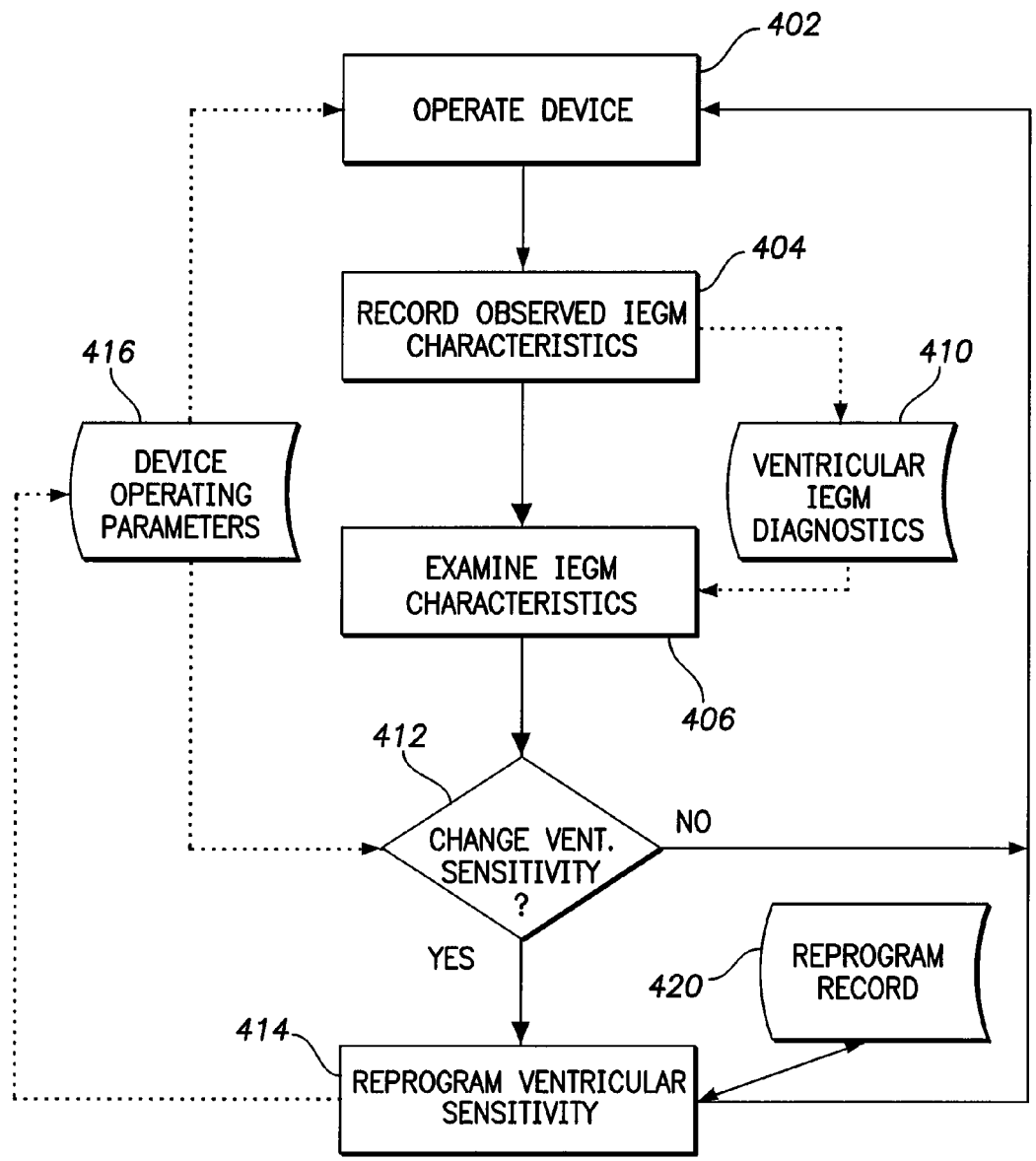
FIG. 9 is a flow chart illustrating an embodiment of the method of FIG. 8 directed to eliminating false-positive detections.

FIG. 9 illustrates exemplary embodiments directed towards improving the performance of device 10. One particular problem that these aspects of the invention address is T-wave oversensing. This can be caused by both early and late sensing of the ventricular depolarization. This can result in persistent fast R sensing as the R-wave is effectively double-sensed with timing being strongly correlated to the prior R wave. This can further result in incorrect tachycardia detection with attendant inappropriate shock delivery and IEGM triggering and storage.

A further potential problem is if the R-wave amplitude decreases or if the sensitivity threshold is set too low, device 10 may fail to correctly detect R-waves. This might lead to an inappropriate determination of a bradycardia condition. This condition can be noted by an increase in the proportion of pacing provided by device 10 to intrinsically triggered beats.

FIG. 9 shows a state 402 indicating normal, ongoing device 10 operation, as previously described. Proceeding therefrom is a state 404 wherein the observed IEGM characteristics (such as pacing proportion, for example) are recorded. State 404 can include recording occurrences and/or frequency of occurrence of detected arrhythmia events. Proceeding therefrom is a state 406 wherein these recorded IEGM characteristics are examined. The examination of state 406 may include, for these embodiments, comparison of recent pacing proportion with either a pre-programmed value and/or a determined value from past device operation. State 406 may also include comparison of an apparent high ventricular rate with data from sensors to determine if patient activity is at a high level (e.g. exercise.) State 406 may also include a comparison between detected P- and R-waves to determine whether or not there is a one-to-one correspondence therebetween, i.e. between detected atrial and ventricular events. Proceeding in parallel is a state 410 wherein the ventricular rate information is diagnosed with the results therefrom contributing to the examination of state 406.

Proceeding from state 406 is a decision state 412 wherein a decision is made whether to change the ventricular sensitivity. A NO decision results in retention of current device 10 programming. A YES decision results in reprogramming of the ventricular sensitivity in state 414 which results in a change of device 10 operating parameters as shown as block 416. An 8-10 mV signal is typically a normal intrinsic signal amplitude. A 3-5 mV signal is typically programmed as device 10 initial sensing threshold. The reprogramming of ventricular sensitivity may be reduced to approximately 0.5 mV; a sensitivity lower than 0.5 mV would typically begin to pick up muscle noise so as to confound the sensing of the R-wave. Reprogramming under state 414 would preferably be performed in stages, e.g. reprogram from a 3 mV sensitivity to 2.5 mV. Device 10 would then return to states 402, 404, 406, and 412 to determine whether the reprogrammed ventricular sensitivity has substantially restored accurate R-sensing or whether additional reprogramming under state 414 is indicated.

Note that the current device 10 operating parameters 416 influence both the operation of the device in state 402 as well as the decision making of state 412. The reprogramming of the ventricular sensitivity in state 414 can be performed under hard rule logic of either inductive or deductive nature or can employ a fuzzy logic methodology. Further, as can be seen in FIG. 9, the reprogramming described above is preferably performed as an ongoing and iterative process.

Interrelated to the reprogramming of state 414 is a recordation state 420. State 420 records the reprogramming history of state 414. The record stored in state 420 is used as an input to the decisions made in state 412 leading to possible reprogramming of state 414. This aspect of the invention inhibits "oscillation" in the reprogramming, i.e. switching back and forth between programming conditions. The decision of state 412 can include whether an excessive amount of reprogramming back and forth is occurring and can disable further reprogramming or impose a time delay before reprogramming is permitted. This aspect also can serve to trigger alternative approaches when it becomes apparent that an oscillation in the programming is indicated. The record of state 420 can also be extracted by a clinician to examine any reprogramming history. This can provide valuable information on possible changes that may have occurred in the patient's condition.

Figure 10:
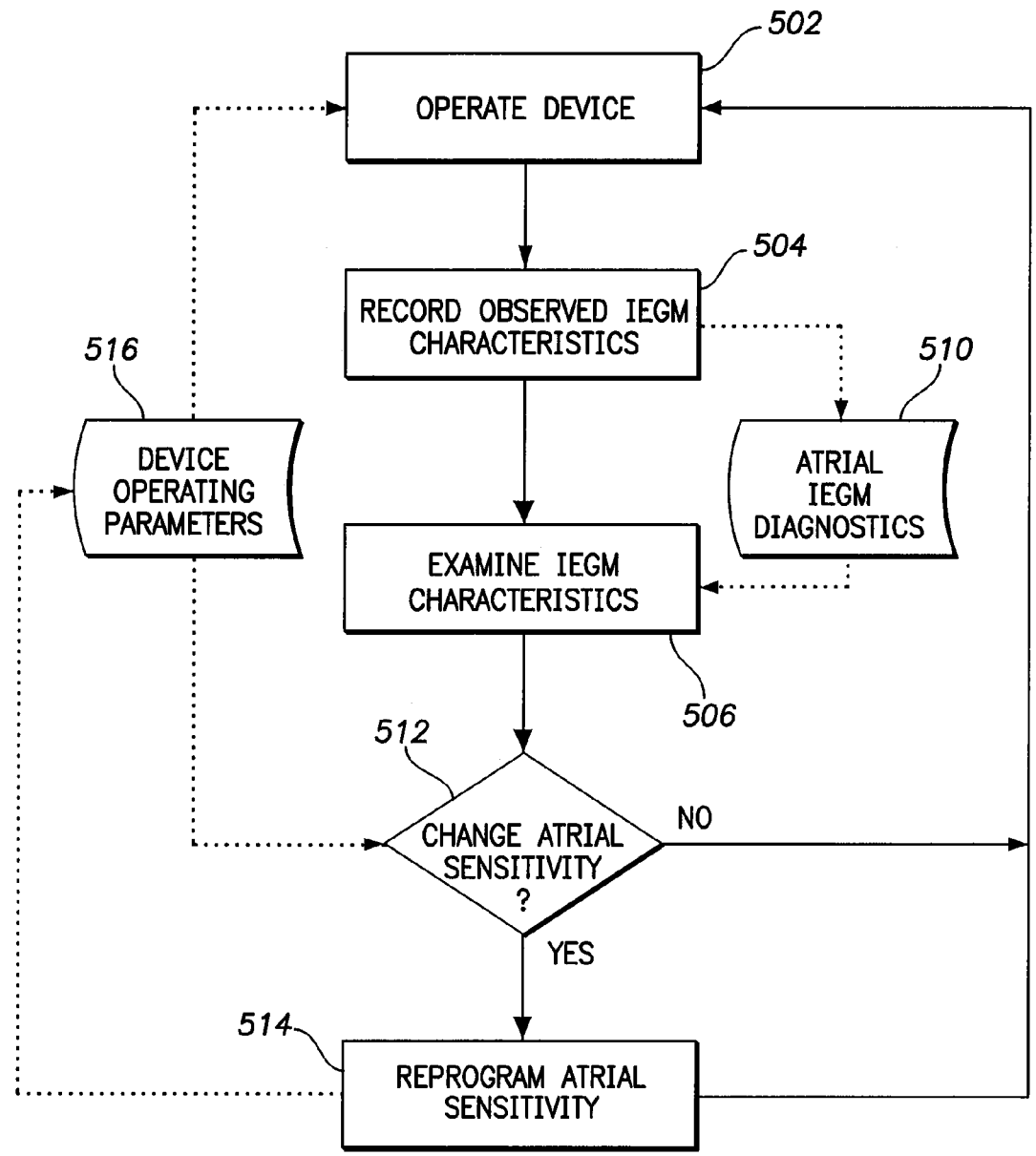
FIG. 10 is a flow chart illustrating an embodiment of the method of FIG. 8 directed to eliminating false-negative detections.

FIG. 10 illustrates exemplary embodiments directed towards avoiding false negatives. These features may be directed, for example, towards reducing the failure to detect AF. This problem might otherwise result in partially missed or completely missed AF detection when intermittent AF is known or expected to be occurring. This concern may be addressed by increasing atrial sensitivity of device 10.

FIG. 10 shows a state 502 indicating normal device 10 operation. Proceeding therefrom is a state 504 wherein the observed IEGM characteristics (for this embodiment this would include detected atrial contractions, rate, etc.) are recorded. Proceeding therefrom is a state 506 wherein these recorded IEGM characteristics are examined. The examination of state 506 would be directed to determining if device 10 appears to be undersensing, e.g. failing to detect events that are assumed to be occurring. For example, if an examination of the patient indicates that intermittent AF is occurring and presumably would continue to occur yet device 10 fails to detect this fibrillation, an increase in the atrial sensitivity might be indicated to allow the device to detect what may be lower amplitude atrial signals.

Another potential occurrence that might indicate that the atrial sensitivity is set too low is detection of a wide variability in the atrial rate. This could be caused by borderline detection of the atrial events such that periodically some of the atrial contractions are not detected, thus leading to a detected atrial rate that is artificially lower than the actual intrinsic activity. A possible confirming factor that can be considered in the examination of state 506 is comparison with other activity sensors to attempt to determine whether a drop in detected rate corresponds to a drop in patient activity level. A further comparison could be made to the detected ventricular events, again assuming a one-to-one correspondence therebetween. State 510 provides for analysis and recording of atrial IEGM information.

Proceeding from the examination of state 506 is a decision state 512 wherein a decision is made whether to change, for example, the atrial sensitivity. A NO decision results in retention of current device 10 programming. A YES decision can result in reprogramming of, in this example, the atrial sensitivity in state 514, which results in a change of device 10 operating parameters as shown as block 516. Upon determination of need for a change in the sensitivity setting, the atrial threshold could be lowered in increments, and the states 502, 504, 506, 512, and possibly 514 are repeated to determine whether satisfactory device 10 operation has been obtained by the new parameters.

It should also be understood that the current device 10 operating parameters 516 influence both the operation of device 10 in state 502 as well as the decision making of state 512. The reprogramming of the atrial sensitivity in state 514 can be performed under hard rule logic of either inductive or deductive nature or can employ a fuzzy logic methodology.

Figure 11:
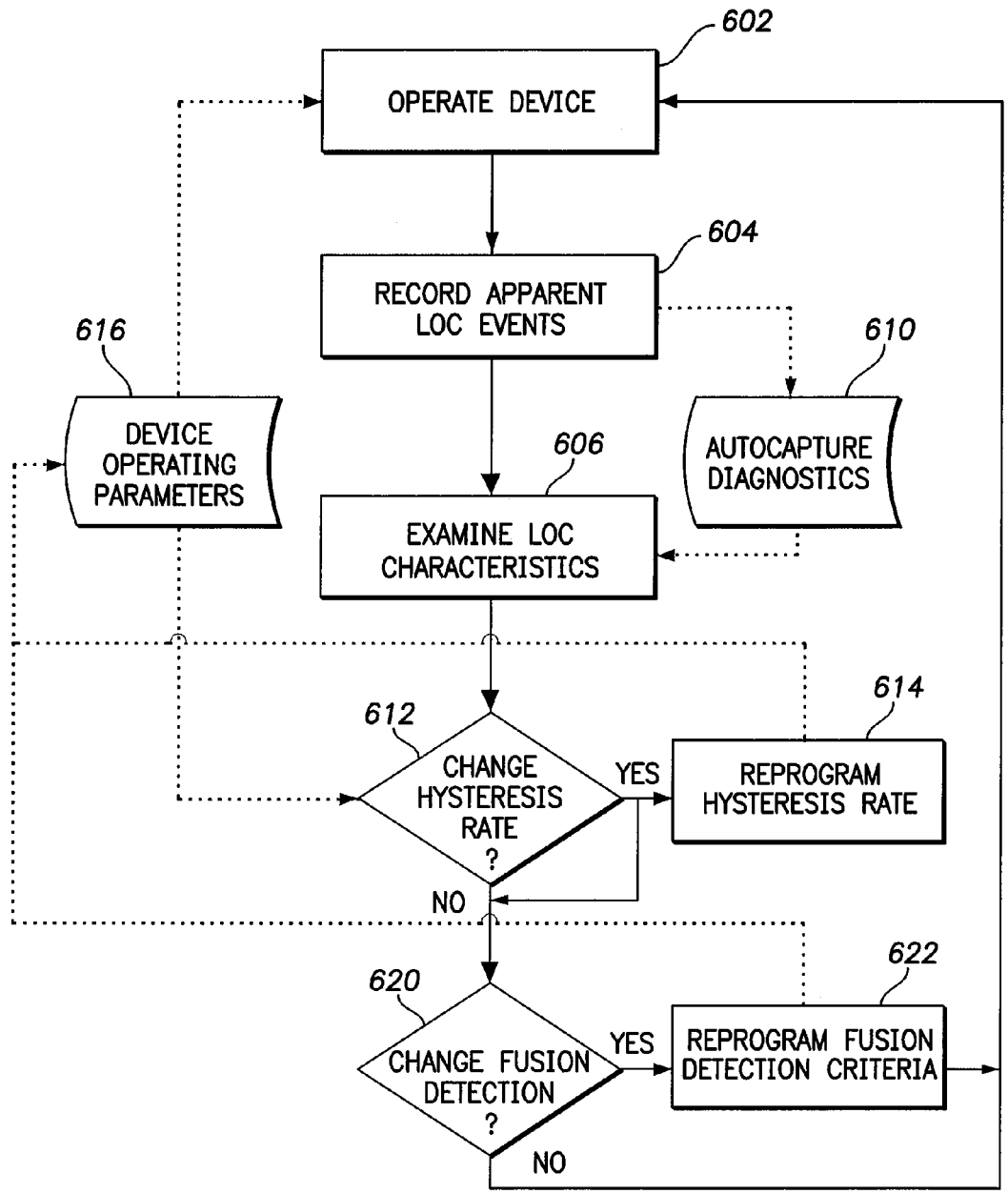
FIG. 11 is a flow chart illustrating an embodiment of the method of FIG. 8 directed to addressing inconclusive/borderline performance issues.

FIG. 11 illustrates exemplary embodiments directed towards improving the performance of device 10 when detecting inconclusive or borderline signals. Particular problems addressed by these aspects of the invention relate to fusion. Fusion in this context refers to cardiac depolarization (atrial or ventricular) resulting from multiple foci. In the context of pacing, fusion generally refers to an observed IEGM waveform resulting when an intrinsic depolarization and a generated output pulse occur simultaneously and thus both contribute to electrical activation of the heart chamber.

In one particular application, a proprietary beat-by-beat pacing system technology, AutoCapture™, automatically verifies capture of each paced beat, adapts the output to changing patient thresholds, and reserves a full-amplitude output as a safety margin. Fusion can cause confounding of the evoked response signals in such systems as the AutoCapture™ resulting in inappropriate back-up pacing and extraneous capture recovery threshold searches. This problem is exhibited as intermittent, yet persistent, back-up pacing and capture recovery searches. The embodiment illustrated in FIG. 11 address these problems by increasing fusion detection sensitivity and/or by increasing fusion tolerance, and/or by enabling/changing the hysteresis rate. The hysteresis, or escape, or hysteresis escape rate is a programmed rate lower than the base rate. The pulse generators can be inhibited if the detected intrinsic rate exceeds the hysteresis rate. Hysteresis is provided to enable the heart 12 to function independently at a reduced rate below the base rate but above the hysteresis rate, but with monitoring by device 10. Should the intrinsic rate drop below the hysteresis rate, one cycle of pacing at the hysteresis rate is typically provided followed by pacing at the base rate until the intrinsic rate is again determined to be above the hysteresis rate.

FIG. 11 shows a state 602 indicating normal device 10 operation. Proceeding therefrom is a state 604 wherein apparent LOC events and fusion occurrences are recorded. Proceeding therefrom is a state 606 wherein the LOC and fusion characteristics are examined. Also optionally occurring in parallel with states 604 and 606 is a state 610 wherein diagnostics are performed as part of the AutoCapture™ system. Proceeding from state 606 is a decision state 612 wherein it is determined whether or not to alter the hysteresis rate. A NO decision will result in retention of the currently set value. A YES decision in state 612 will lead to state 614 wherein the hysteresis rate is reprogrammed. The function of device 10 and the intrinsic activity of the heart 12 would then continue to be examined in state 606 to determine whether a further change in the hysteresis rate is indicated. As previously described, the operating parameters, such as the hysteresis rate, can be iteratively adjusted until desired operation is achieved.

Further proceeding from state 612 is another decision state 620 wherein a decision is made whether or not to change the fusion detection criteria in a state 622. Reprogramming the fusion detection criteria can include changing the upper and/or lower limits for the negative area under the curve following a pacing pulse to establish fusion occurrence. A NO decision will result in retention of current device 10 programming. A NO decision can also result in e.g. speeding up the pacing rate to confirm capture. A YES decision may trigger a capture threshold search to reestablish a capture threshold. A YES decision may also result in a change in the number and/or frequency of apparent LOC events to trigger a capture threshold search.

Figure 12:
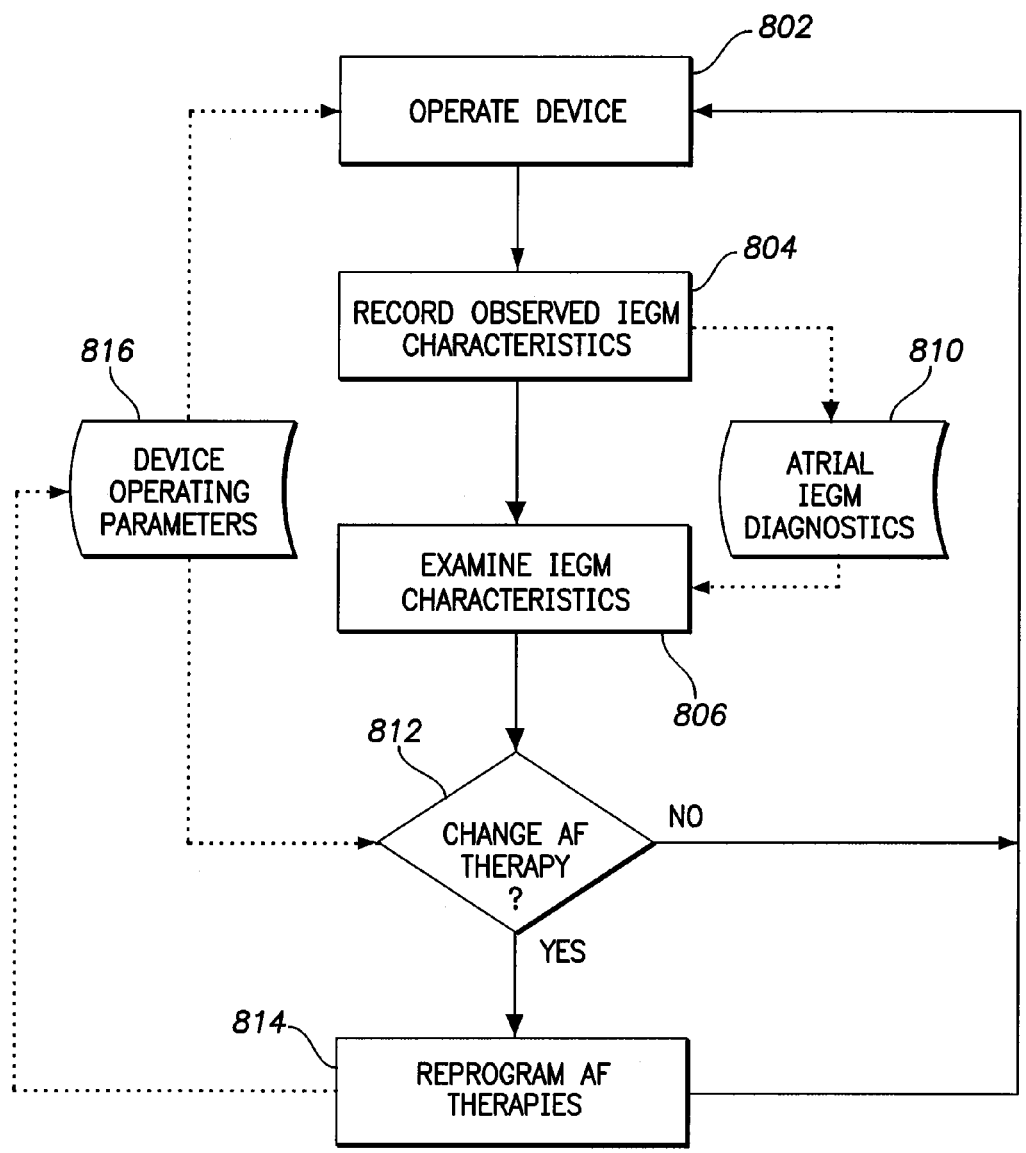
FIG. 12 is a flow chart illustrating an embodiment of the method of FIG. 8 directed to improving atrial arrhythmia therapy.

FIG. 12 illustrates exemplary embodiments directed towards improving the performance of device 10 in situations where the patient condition changes during the implantation period. For example, a patient may spontaneously develop AF events after implantation of device 10 where none were observed prior to implantation or in previous check-up visits. Device 10 typically is provided with a plurality of therapy programs, all of which are often not enabled at implantation. Thus, prior programming of appropriate therapies to address the AF is available in device 10, however, was not made as it was not indicated at the time.

This particular issue manifests as intermittent runs of high, irregular atrial rates. One response of device 10, according to one aspect of the invention, is to enable device mode switching and set a trigger rate on recent atrial rate diagnostics. Alternatively, or in addition, device 10 may enable Dynamic Atrial Overdriven™ (DAO) pacing to suppress the progression of the AF. Overdrive pacing refers to programming the base rate higher than the patient's intrinsic rhythm, thereby causing the pulse generator to pace all the time. In overdrive pacing, the pulse generator gains control of the heart 12, which can be effective in terminating or inhibiting certain tachycardias and other arrhythmias. For example, with an intrinsic rate of 80 bpm, device 10 can overdrive via pacing at a rate of 85 bpm and periodically drop down the paced rate to confirm the intrinsic rate and return to overdrive pacing.

FIG. 12 shows a state 802 indicating normal ongoing device 10 operation. Proceeding therefrom is a state 804 wherein the observed rate characteristics are recorded (in this embodiment, the atrial events). Proceeding therefrom is a state 806 wherein these recorded rate characteristics are examined. In this embodiment, the examination of state 806 is directed to examining the current atrial rate characteristics and comparing these to past records. The examination of state 806 may indicate that atrial fibrillation appears to be occurring, at least intermittently, at present, but had not been previously detected. In state 810, the atrial rate information is analyzed and recorded with the results therefrom contributing to the examination of state 806.

Proceeding from state 806 is a decision state 812 wherein a decision is made to change the atrial fibrillation therapy. A NO decision results in retention of current device 10 programming, which, in this aspect, would not have DAO pacing enabled. A YES decision may result in reprogramming of the atrial fibrillation therapies in state 814, which results in a change of device 10 operating parameters as shown as block 816. In particular, the decision of state 812 in the situation illustrated in this embodiment would result in a reprogramming in state 814 including enabling DAO pacing where this therapy was not previously enabled. The reprogramming of state 814 can also include changing the atrial rate that triggers a switch between therapy modes of device 10. For example, the detected atrial rate at which fibrillation onset has occurred can be changed. The device 10 operating parameters 816 influence both the operation of device 10 in state 802 as well as the decision making of state 812.

Aspects of the operation of exemplary embodiments of device 10 have been described with reference to the state diagrams of FIGS. 8-12. These features may be implemented independently of one another or in parallel operation in any possible combination in specific applications and embodiments. It should also to be understood that other operational aspects of device 10, including those previously described with reference can operate separately, or in parallel with, or in the absence of, the features described with reference to FIGS. 8-12.

Off-Line Reprogramming Performed by External System

Figure 13:
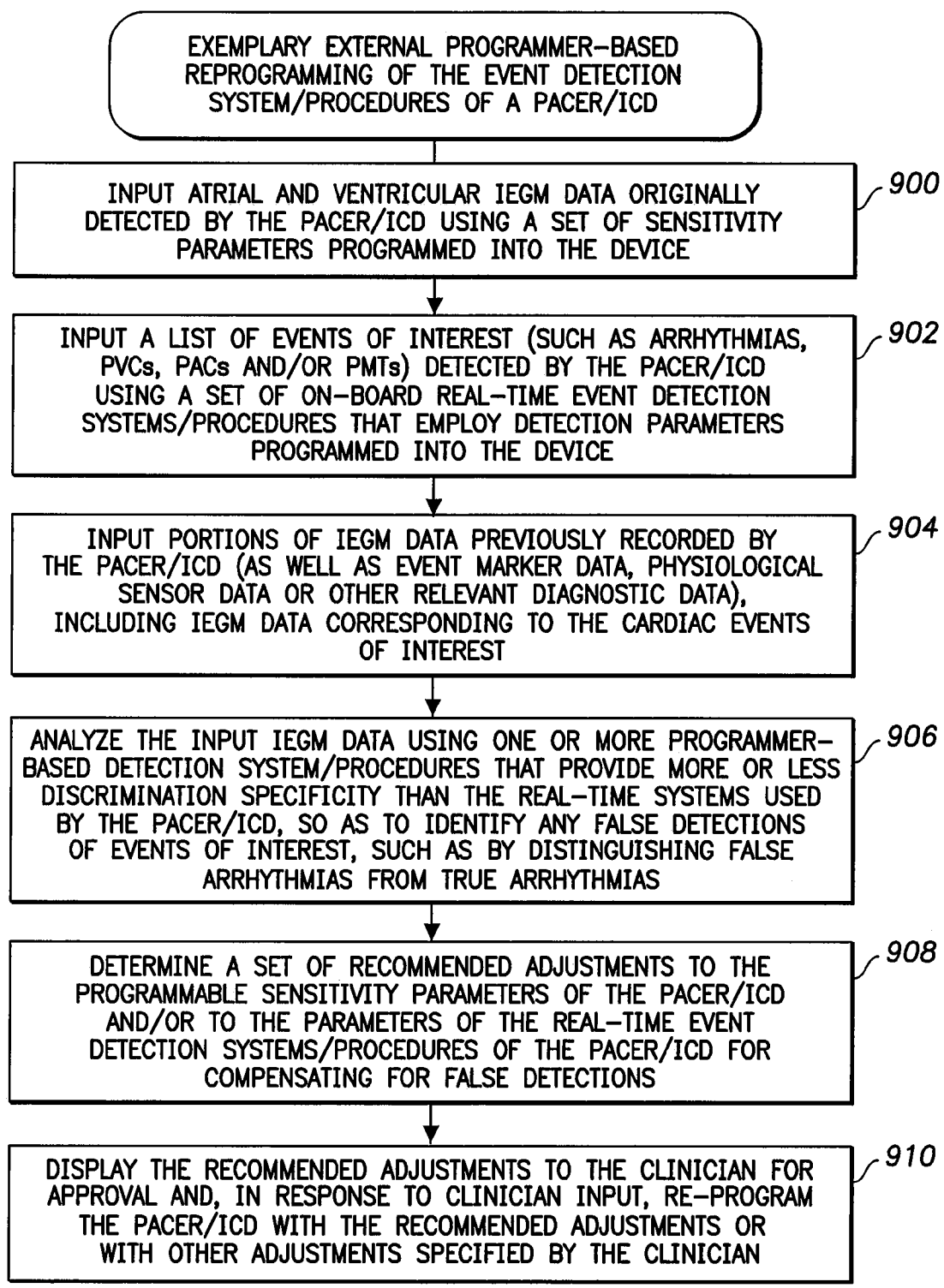
FIG. 13 illustrates an alternative implementation of the technique of FIG. 2 wherein the off-line analysis is performed by an external system.

Turning now to FIG. 13, techniques will now be summarized for off-line analysis employing an external system such as a device programmer or bedside monitor. Many of these steps are the same or similar to steps performed by the implantable device of the preceding examples and hence will not be described in detail again.

Beginning at step 900, the external system inputs atrial and ventricular IEGM data originally detected by the pacer/ICD using a set of sensitivity parameters previously programmed into the device. At step 902, the external system inputs a list of events of interest (such as arrhythmias, PVCs, PACs and/or PMTs or other abnormal cardiac events) detected by the pacer/ICD using a set of on-board real-time event detection systems/procedures that employ detection parameters previously programmed into the device. At step 904, the external system inputs portions of IEGM data previously recorded by the pacer/ICD (as well as event marker data, physiological sensor data or other relevant diagnostic data), including IEGM data portions corresponding to the cardiac events of interest, such as pre-trigger and post-trigger data and any other recorded IEGM data.

At step 906, the external system analyzes the input IEGM data using one or more programmer-based detection system/procedures that provide more or less discrimination specificity than the real-time systems used by the pacer/ICD, so as to identify any false detections of events of interest, such as by distinguishing false arrhythmias from true arrhythmias. This may exploit techniques similar to those of step 214 of FIG. 4 but implemented by the external system. At step 908, the external system determines a set of recommended adjustments to the programmable sensitivity parameters of the pacer/ICD and/or to the parameters of the real-time event detection systems/procedures of the pacer/ICD for compensating for false detections. This may exploit techniques similar to those of FIGS. 5-7 but implemented by the external system. At step 910, the external system (assuming it is so equipped) then displays the recommended adjustments to the clinician for approval and, in response to clinician input, the external system re-programs the pacer/ICD with the recommended adjustments or with other adjustments specified by the clinician. Alternatively, the external system can automatically reprogram the pacer/ICD without clinician approval, as may be appropriate if the external system is a bedside monitor or the like.

Although primarily described with respect to examples wherein the implantable device is a pacer/ICD, other implantable medical devices may be equipped to exploit the techniques described herein such as cardiac resynchronization therapy (CRT) devices and CRT-D devices. For the sake of completeness, an exemplary pacer/ICD will now be described, which includes components for performing the functions and steps already described.

Exemplary Pacer/ICD

Figure 14:
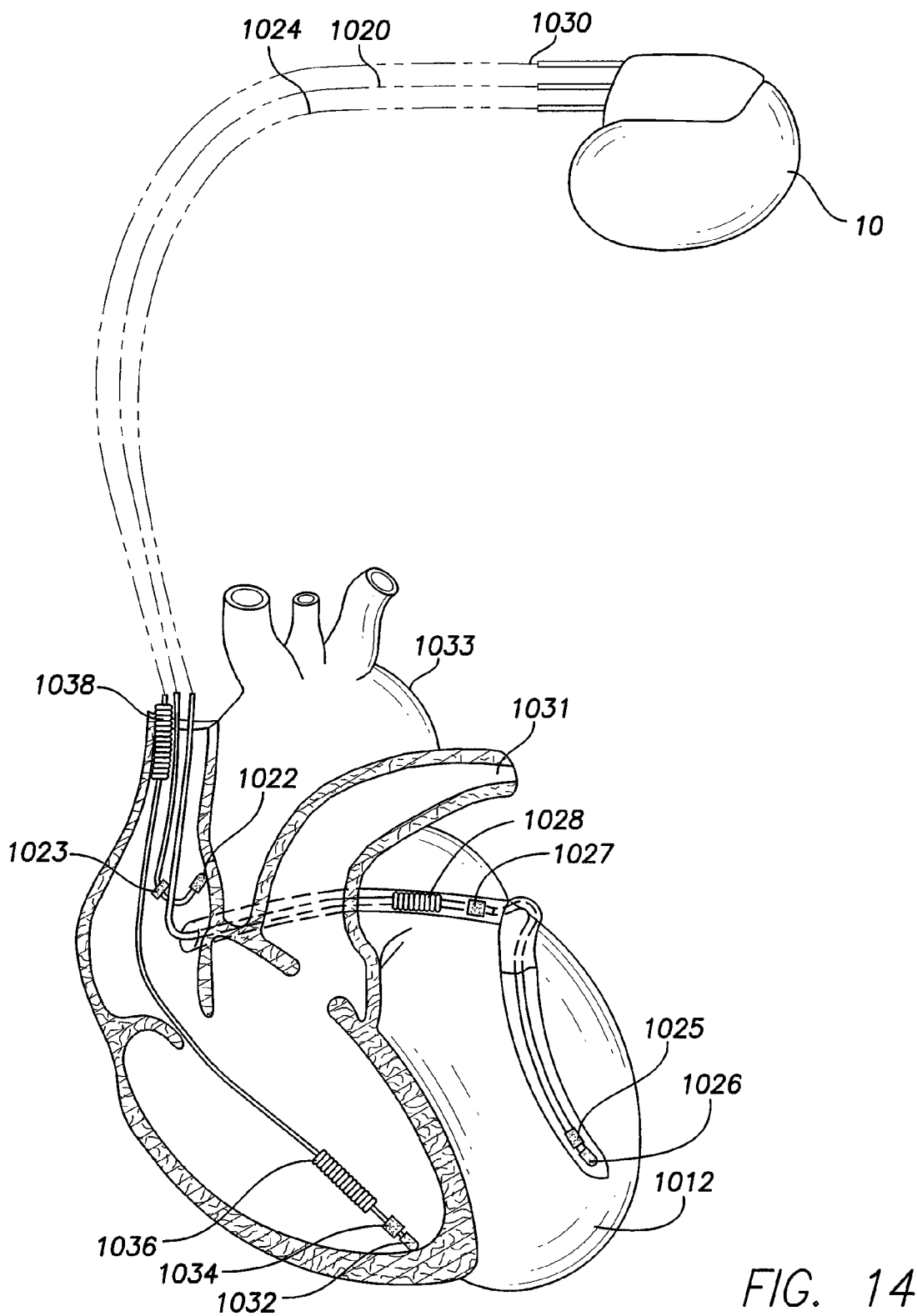
FIG. 14 is a simplified, partly cutaway view, illustrating the pacer/ICD of FIG. 1 along with a set of leads implanted into the heart of the patient.
Figure 15:
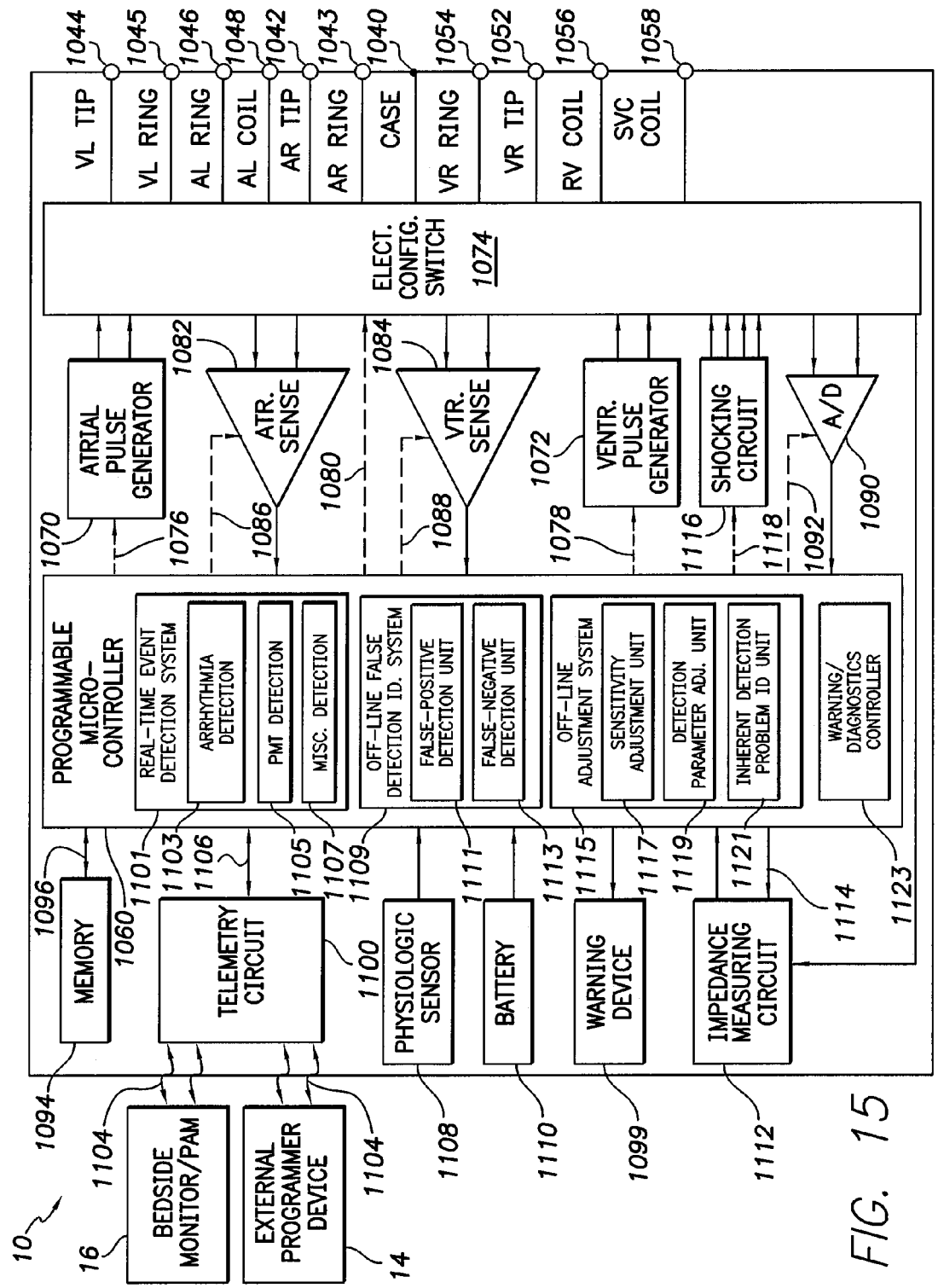
FIG. 15 is a functional block diagram of the pacer/ICD of FIG. 14, illustrating basic circuit elements that provide cardioversion, defibrillation and/or pacing stimulation in the heart an particularly illustrating an on-board off-line analysis system for performing the techniques of FIGS. 2-12.

With reference to FIGS. 14 and 15, a description of an exemplary pacer/ICD will now be provided. FIG. 14 provides a simplified block diagram of the pacer/ICD, which is a dual-chamber stimulation device capable of treating both fast and slow arrhythmias with stimulation therapy, including cardioversion, defibrillation, and pacing stimulation, and also capable of setting and using VV pacing delays, as discussed above. To provide other atrial chamber pacing stimulation and sensing, pacer/ICD 10 is shown in electrical communication with a heart 1012 by way of a left atrial lead 1020 having an atrial tip electrode 1022 and an atrial ring electrode 1023 implanted in the atrial appendage. Pacer/ICD 10 is also in electrical communication with the heart by way of a right ventricular lead 1030 having, in this embodiment, a ventricular tip electrode 1032, a right ventricular ring electrode 1034, a right ventricular (RV) coil electrode 1036, and a superior vena cava (SVC) coil electrode 1038. Typically, the right ventricular lead 1030 is transvenously inserted into the heart so as to place the RV coil electrode 1036 in the right ventricular apex, and the SVC coil electrode 1038 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a CS lead 1024 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 1024 is designed to receive atrial and ventricular cardiac signals and to deliver left ventricular pacing therapy using at least a left ventricular tip electrode 1026 and a LV ring electrode 1025, left atrial pacing therapy using at least a left atrial ring electrode 1027, and shocking therapy using at least a left atrial coil electrode 1028. With this configuration, biventricular pacing can be performed. Although only three leads are shown in FIG. 14, it should also be understood that additional leads (with one or more pacing, sensing and/or shocking electrodes) might be used and/or additional electrodes might be provided on the leads already shown.

A simplified block diagram of internal components of pacer/ICD 10 is shown in FIG. 15. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 1040 for pacer/ICD 10, shown schematically in FIG. 15, is often referred to as the "can", "case" or "case electrode" and may be programmably selected to act as the return electrode for all "unipolar" modes. The housing 1040 may further be used as a return electrode alone or in combination with one or more of the coil electrodes, 1028, 1036 and 1038, for shocking purposes. The housing 1040 further includes a connector (not shown) having a plurality of terminals, 1042, 1043, 1044, 1045, 1046, 1048, 1052, 1054, 1056 and 1058 (shown schematically and, for convenience, the names of the electrodes to which they are connected are shown next to the terminals). As such, to achieve right atrial sensing and pacing, the connector includes at least a right atrial tip terminal ($A_R$ TIP) 1042 adapted for connection to the atrial tip electrode 1022 and a right atrial ring ($A_R$ RING) electrode 1043 adapted for connection to right atrial ring electrode 1023. To achieve left chamber sensing, pacing and shocking, the connector includes at least a left ventricular tip terminal ($V_L$ TIP) 1044, a left ventricular ring terminal ($V_L$ RING) 1045, a left atrial ring terminal ($A_L$ RING) 1046, and a left atrial shocking terminal ($A_L$ COIL) 1048, which are adapted for connection to the left ventricular ring electrode 1026, the left atrial ring electrode 1027, and the left atrial coil electrode 1028, respectively. To support right chamber sensing, pacing and shocking, the connector further includes a right ventricular tip terminal ($V_R$ TIP) 1052, a right ventricular ring terminal ($V_R$ RING) 1054, a right ventricular shocking terminal ($V_R$ COIL) 1056, and an SVC shocking terminal (SVC COIL) 1058, which are adapted for connection to the right ventricular tip electrode 1032, right ventricular ring electrode 1034, the $V_R$ coil electrode 1036, and the SVC coil electrode 1038, respectively.

At the core of pacer/ICD 10 is a programmable microcontroller 1060, which controls the various modes of stimulation therapy. As is well known in the art, the microcontroller 1060 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 1060 includes the ability to process or monitor input signals (data) as controlled by a program code stored in a designated block of memory. The details of the design and operation of the microcontroller 1060 are not critical to the invention. Rather, any suitable microcontroller 1060 may be used that carries out the functions described herein. The use of microprocessor-based control circuits for performing timing and data analysis functions are well known in the art.

As shown in FIG. 15, an atrial pulse generator 1070 and a ventricular pulse generator 1072 generate pacing stimulation pulses for delivery by the right atrial lead 1020, the right ventricular lead 1030, and/or the CS lead 1024 via an electrode configuration switch 1074. It is understood that in order to provide stimulation therapy in each of the four chambers of the heart, the atrial and ventricular pulse generators, 1070 and 1072, may include dedicated, independent pulse generators, multiplexed pulse generators or shared pulse generators. The pulse generators, 1070 and 1072, are controlled by the microcontroller 1060 via appropriate control signals, 1076 and 1078, respectively, to trigger or inhibit the stimulation pulses.

The microcontroller 1060 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 1074 includes a plurality of switches for connecting the desired electrodes to the appropriate I/O circuits, thereby providing complete electrode programmability. Accordingly, the switch 1074, in response to a control signal 1080 from the microcontroller 1060, determines the polarity of the stimulation pulses (e.g., unipolar, bipolar, combipolar, etc.) by selectively closing the appropriate combination of switches (not shown) as is known in the art.

Atrial sensing circuits 1082 and ventricular sensing circuits 1084 may also be selectively coupled to the right atrial lead 1020, CS lead 1024, and the right ventricular lead 1030, through the switch 1074 for detecting the presence of cardiac activity in each of the four chambers of the heart. Accordingly, the atrial (ATR. SENSE) and ventricular (VTR. SENSE) sensing circuits, 1082 and 1084, may include dedicated sense amplifiers, multiplexed amplifiers or shared amplifiers. The switch 1074 determines the "sensing polarity" of the cardiac signal by selectively closing the appropriate switches, as is also known in the art. In this way, the clinician may program the sensing polarity independent of the stimulation polarity. Each sensing circuit, 1082 and 1084, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 1082 and 1084, are connected to the microcontroller 1060 which, in turn, are able to trigger or inhibit the atrial and ventricular pulse generators, 1070 and 1072, respectively, in a demand fashion in response to the absence or presence of cardiac activity in the appropriate chambers of the heart.

For arrhythmia detection, pacer/ICD 10 utilizes the atrial and ventricular sensing circuits, 1082 and 1084, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 1060 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 1090. The data acquisition system 1090 is configured to acquire intracardiac electrogram signals, convert the raw analog data into a digital signal, and store the digital signals for later processing and/or telemetric transmission to an external device 1102. The data acquisition system 1090 is coupled to the right atrial lead 1020, the CS lead 1024, and the right ventricular lead 1030 through the switch 1074 to sample cardiac signals across any pair of desired electrodes. The microcontroller 1060 is further coupled to a memory 1094 by a suitable data/address bus 1096, wherein the programmable operating parameters used by the microcontroller 1060 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 1094 through a telemetry circuit 1100 in telemetric communication with an external device, such as a programmer 14, bedside monitor 16, transtelephonic transceiver or a diagnostic system analyzer or other external system. The telemetry circuit 1100 is activated by the microcontroller by a control signal 1106. The telemetry circuit 1100 advantageously allows intracardiac electrograms and status information relating to the operation of pacer/ICD 10 (as contained in the microcontroller 1060 or memory 1094) to be sent to the external device 1102 through an established communication link 1104. Pacer/ICD 10 further includes an accelerometer or other physiologic sensor 1108, commonly referred to as a "rate-responsive" sensor because it is typically used to adjust pacing stimulation rate according to the exercise state of the patient. However, the physiological sensor 1108 may further be used to detect changes in cardiac output, changes in the physiological condition of the heart, or diurnal changes in activity (e.g., detecting sleep and wake states) and to detect arousal from sleep. Accordingly, the microcontroller 1060 responds by adjusting the various pacing parameters (such as rate, AV delay, VV delay, etc.) at which the atrial and ventricular pulse generators, 1070 and 1072, generate stimulation pulses. While shown as being included within pacer/ICD 10, it is to be understood that the physiologic sensor 1108 may also be external to pacer/ICD 10, yet still be implanted within or carried by the patient. A common type of rate responsive sensor is an activity sensor incorporating an accelerometer or a piezoelectric crystal, which is mounted within the housing 1040 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 1110, which provides operating power to all of the circuits shown in FIG. 15. The battery 1110 may vary depending on the capabilities of pacer/ICD 10. If the system only provides low voltage therapy, a lithium iodine or lithium copper fluoride cell typically may be utilized. For pacer/ICD 10, which employs shocking therapy, the battery 1110 should be capable of operating at low current drains for long periods, and then be capable of providing high-current pulses (for capacitor charging) when the patient requires a shock pulse. The battery 1110 should also have a predictable discharge characteristic so that elective replacement time can be detected. Accordingly, appropriate batteries are employed.

As further shown in FIG. 15, pacer/ICD 10 is shown as having an impedance measuring circuit 1112, which is enabled by the microcontroller 1060 via a control signal 1114. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 1112 is advantageously coupled to the switch 1174 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 1060 further controls a shocking circuit 1116 by way of a control signal 1118. The shocking circuit 1116 generates shocking pulses of low (up to 0.5 joules), moderate (0.5-10 joules) or high energy (11 to 40 joules), as controlled by the microcontroller 1060. Such shocking pulses are applied to the heart of the patient through at least two shocking electrodes, and as shown in this embodiment, selected from the left atrial coil electrode 1028, the RV coil electrode 1036, and/or the SVC coil electrode 1038. The housing 1040 may act as an active electrode in combination with the RV electrode 1036, or as part of a split electrical vector using the SVC coil electrode 1038 or the left atrial coil electrode 1028 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 11-40 joules), delivered asynchronously (since R-waves may be too disorganized), and pertaining exclusively to the treatment of fibrillation. Accordingly, the microcontroller 1060 is capable of controlling the synchronous or asynchronous delivery of the shocking pulses.

An internal warning device 1099 may be provided for generating perceptible warning signals to the patient via vibration, voltage or other methods.

Insofar as off-line analysis and reprogramming is concerned, microcontroller 1060 includes a real-time cardiac event detection system 1101 that detects cardiac events of interest substantially in real-time, such as abnormal events. The detection system includes an arrhythmia detection unit 1103, a PMT detection unit 1105 and a miscellaneous event detection unit 1107 for detecting other events of interest such as PACs, PVCs, LOC events, AMS events, etc. Indications of the cardiac events of interest and corresponding IEGM data are stored in memory 1094.

An off-line false detection identification system 1109 is operative to subsequently retrieve and analyze recorded IEGM to identify false detections of events of interest within the patient in accordance with the various false event identification techniques described above. To this end, system 1109 includes a false-positive detection unit 1111 and a false-negative detection unit 1113. An off-line adjustment system 1115 is operative to selectively adjust one or both of the cardiac signal sensing system of the pacer/ICD and event detection system 1103 to reduce false detections of events of interest, in accordance with the various reprogramming or adjustment techniques described above. To this end, system 1115 includes a sensitivity adjustment unit 1117, a detection parameter adjustment unit 1119, and an inherent detection problem identification unit 1121.

A warning/diagnostics controller 1123 is provided to generate any needed warnings, such as warning indicative of an inherent detection problem, and to record diagnostics pertaining to the off-line analysis, such as in indication of any adjustments made to the various sensitivity/detection parameters.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

As noted, at least some of the techniques described herein can be performed by (or under the control of) an external device. For the sake of completeness, an exemplary device programmer will now be described, which includes components for controlling at least some of the functions and steps already described.

Exemplary External Programmer

Figure 16:
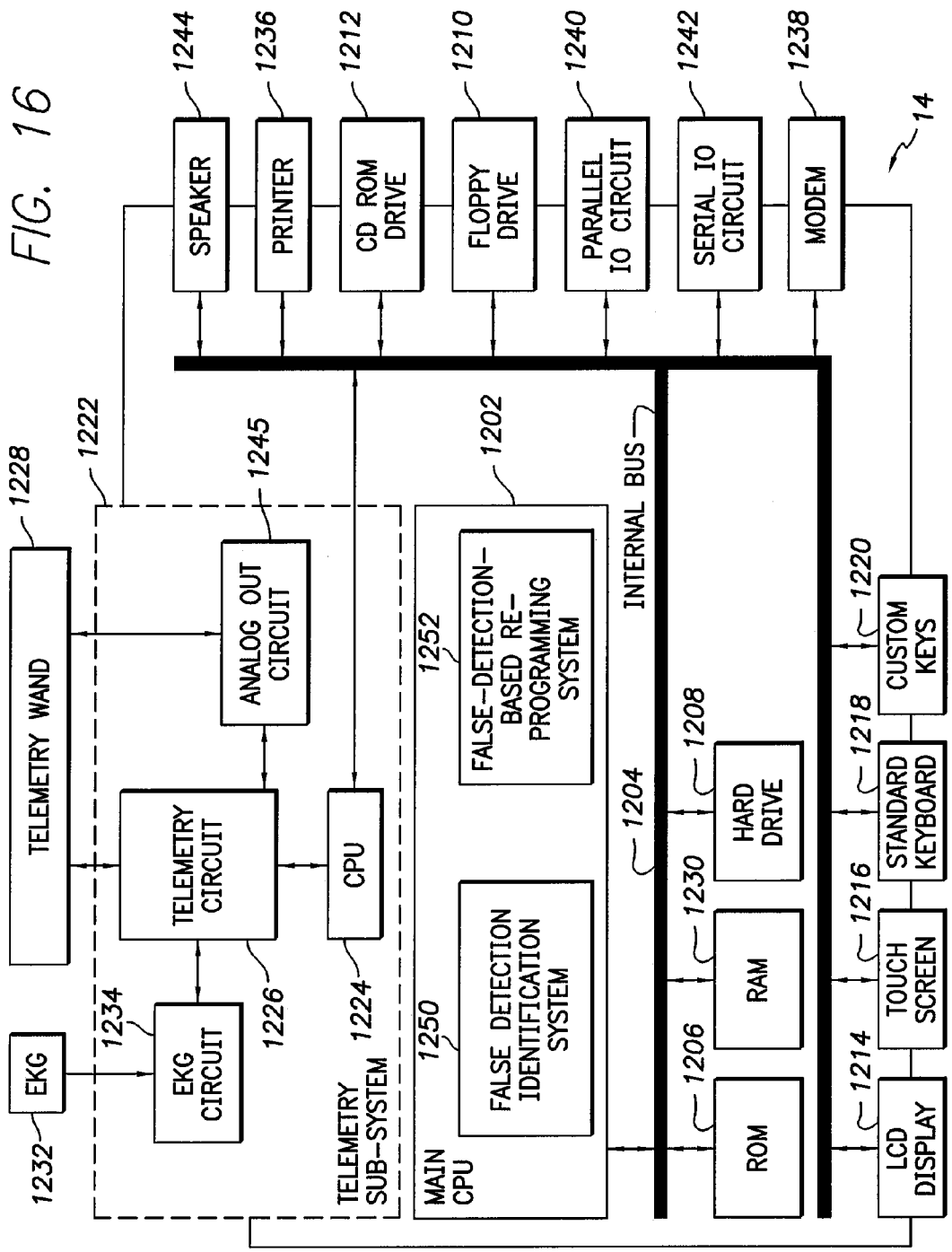
FIG. 16 is a functional block diagram illustrating components of the external device programmer of FIG. 1, and in particular illustrating a programmer-based off-line analysis system for performing or controlling at least some of the techniques of FIGS. 2-12.

FIG. 16 illustrates pertinent components of an external programmer 14 for use in programming the pacer/ICD of FIG. 15 and for performing the above-described off-line analysis techniques. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 14 may also be capable of processing and analyzing data received from the implanted device and from the EKG leads to, for example, render preliminary diagnosis as to medical conditions of the patient or to the operations of the implanted device.

Now, considering the components of programmer 14, operations of the programmer are controlled by a CPU 1202, which may be a generally programmable microprocessor or microcontroller or may be a dedicated processing device such as an application specific integrated circuit (ASIC) or the like. Software instructions to be performed by the CPU are accessed via an internal bus 1204 from a read only memory (ROM) 1206 and random access memory 1230. Additional software may be accessed from a hard drive 1208, floppy drive 1210, and CD ROM drive 1212, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 1214 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 1216 overlaid on the LCD display or through a standard keyboard 1218 supplemented by additional custom keys 1220, such as an emergency VVI (EVVI) key. The EVVI key sets the implanted device to a safe VVI mode with high pacing outputs. This ensures life sustaining pacing operation in nearly all situations but by NO means is it desirable to leave the implantable device in the EVVI mode at all times.

Once all pacing leads are mounted and the pacing device is implanted, the various parameters are programmed. Typically, the physician initially controls the programmer 14 to retrieve data stored within any implanted devices and to also retrieve EKG data from EKG leads, if any, coupled to the patient. To this end, CPU 1202 transmits appropriate signals to a telemetry subsystem 1222, which provides components for directly interfacing with the implanted devices, and the EKG leads. Telemetry subsystem 1222 includes its own separate CPU 1224 for coordinating the operations of the telemetry subsystem. Main CPU 1202 of programmer communicates with telemetry subsystem CPU 1224 via internal bus 1204. Telemetry subsystem additionally includes a telemetry circuit 1226 connected to telemetry wand 1228, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 1234 for receiving surface EKG signals from a surface EKG system 1232. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 14 either within a random access memory (RAM) 1230, hard drive 1208 or within a floppy diskette placed within floppy drive 1210. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 14, the implanted devices may be further controlled to transmit additional data in real time as it is detected by the implanted devices, such as additional IEGM data, lead impedance data, and the like. Additionally, or in the alternative, telemetry subsystem 1222 receives EKG signals from EKG leads 1232 via an EKG processing circuit 1234. As with data retrieved from the implanted device itself, signals received from the EKG leads are stored within one or more of the storage devices of the external programmer. Typically, EKG leads output analog electrical signals representative of the EKG. Accordingly, EKG circuit 1234 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 1202, the programming commands are converted to specific programmable parameters for transmission to the implanted devices via telemetry wand 1228 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 1236.

Insofar as off-line analysis and reprogramming is concerned, CPU 1202 also preferably includes a false detection identification system 1250 that is operative to retrieve and analyze recorded IEGM data from the pacer/ICD and to identify false detections of events of interest within the patient generally in accordance with the various false event identification techniques, described above. A false-detection-based re-programming system 1252 is provided that is operative to selectively adjust one or both of the cardiac signal sensing system of the pacer/ICD and event detection system of the pacer/ICD to reduce false detections of events of interest, generally in accordance with the various reprogramming or adjustment techniques described above. Adjusted pacing parameters and/or other control information is then transmitted to the pacer/ICD under the control of the telemetry subsystem.

Programmer/monitor 14 also includes a modem 1238 to permit direct transmission of data to other programmers via the public switched telephone network (PSTN) or other interconnection line, such as a T1 line or fiber optic cable. Depending upon the implementation, the modem may be connected directly to internal bus 1204 may be connected to the internal bus via either a parallel port 1240 or a serial port 1242. Other peripheral devices may be connected to the external programmer via parallel port 1240 or a serial port 1242 as well. Although one of each is shown, a plurality of input output (IO) ports might be provided. A speaker 1244 is included for providing audible tones to the user, such as a warning beep in the event improper input is provided by the physician. Telemetry subsystem 1222 additionally includes an analog output circuit 1245 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted devices and to reprogram the implanted device if needed. The descriptions provided herein with respect to FIG. 16 are intended merely to provide an overview of the operation of programmer and are not intended to describe in detail every feature of the hardware and software of the programmer and is not intended to provide an exhaustive list of the functions performed by the programmer.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical device, the method comprising:
    sensing a cardiac signal within a patient in which the implantable medical device is implanted using a cardiac signal sensing system of the implantable medical device;
    detecting cardiac events of interest within the patient using an event detection system of the implantable medical device;
    recording portions of the cardiac signal, including portions representative of the events of interest;
    detecting a stable cardiac state of the patient by the implantable medical device;
    in response to detecting the stable cardiac state, initiating an off-line analysis of the recorded portions of the cardiac signal including portions representative of events of interest to identify false detections of events of interest, wherein the off-line analysis is performed by the implantable medical device concurrently with continued operation of the event detection system; and
    selectively adjusting one or both of the cardiac signal sensing system and the event detection system to reduce false detections of events of interest identified by the off-line analysis.

2. The method of claim 1 wherein the events of interest are abnormal cardiac events.

3. The method of claim 2 wherein the abnormal cardiac events include one or more of: arrhythmia events, premature atrial contraction (PAC) events, premature ventricular contraction (PVC) events, pacemaker mediated tachycardia (PMT) events and automatic mode switching (AMS) events.

4. The method of claim 1 wherein the false detections include one or both of false-positive detections and false-negative detections.

5. The method of claim 1 wherein detecting cardiac events of interest within the patient using the event detection system is performed substantially in real-time.

6. The method of claim 1 wherein retrieving and analyzing the portions of the cardiac signal to identify false detections of events of interest includes: analyzing patient cardiac signals using an alternative event detection system that is less discriminating so as to identify possible false-negative detections.

7. The method of claim 1 wherein retrieving and analyzing the portions of the cardiac signal to identify false detections of events includes: detecting the relative timing of event detections and exploiting the relative timing to distinguish between false detections and true detections.

8. The method of claim 1 wherein the event detection system exploits at least one adjustable detection parameter and wherein the detection parameter is adjusted to reduce false detections.

9. The method of claim 1 wherein the false detection is a false-negative detection and wherein the detection parameter is adjusted to expand a range of event detection to thereby reduce false-negative detections.

10. The method of claim 1 wherein the false detection is a false-positive detection and wherein the detection parameter is adjusted to reduce a range of event detection to thereby reduce false-positive detections.

11. The method of claim 1 wherein the cardiac signal sensing system exploits at least one sensitivity parameter and wherein the sensitivity parameter is adjusted to improve event detection by improving the sensing of cardiac signals used to detect events of interest.

12. The method of claim 1 wherein selectively adjusting the abnormal event detection system to reduce false detections of events of interest includes: repeatedly reapplying the recorded cardiac signal data from the patient to an off-line event detection system along with an indication of false event detections while adjusting parameters employed by the off-line detection system so as to determine a set of detection parameters sufficient to reduce false detections.

13. The method of claim 1 wherein selectively adjusting the event detection system to reduce false detections of events of interest includes controlling a rate at which parameters employed by the detection system are iteratively adjusted.

14. The method of claim 1 wherein selectively adjusting the event detection system to reduce false detections of events of interest includes controlling a maximum range through which parameters employed by the detection system are adjusted.

15. The method of claim 1 wherein selectively adjusting the event detection system to reduce false detections of events of interest includes employing a history of prior adjustments to control subsequent adjustments.

16. The method of claim 1 wherein, upon detecting an inherent limitation in the event detection system, the device selectively adjusts a degree of bias between false-positive and false-negative events.

17. The method of claim 16 wherein, upon detecting an inherent limitation in the event detection system, the device generates a warning.

18. The method of claim 16 wherein, upon detecting an inherent limitation in the event detection system, the device reverts to a previous parameter setting.

19. The method of claim 16 wherein, upon detecting an inherent limitation in the event detection system, the device evaluates the severity of events of interest and selectively inhibits the recording of cardiac signal data based on severity.

20. The method of claim 1 further comprising: detecting whether a sufficient amount of available processor capacity is available to perform the off-line analysis.

* * * * *